United States Patent
Niroula et al.

(10) Patent No.: US 12,424,302 B2
(45) Date of Patent: Sep. 23, 2025

(54) ACCELERATED MOLECULAR DYNAMICS SIMULATION METHOD ON A QUANTUM-CLASSICAL HYBRID COMPUTING SYSTEM

(71) Applicant: IONQ, INC., College Park, MD (US)

(72) Inventors: Pradeep Niroula, College Park, MD (US); Wengang Zhang, Gaithersburg, MD (US); Yunseong Nam, North Bethesda, MD (US)

(73) Assignee: IONQ, INC., College Park, MD (US)

(*) Notice: Subject to any disclaimer, the term of this patent is extended or adjusted under 35 U.S.C. 154(b) by 1275 days.

(21) Appl. No.: 17/162,566

(22) Filed: Jan. 29, 2021

(65) Prior Publication Data

US 2021/0233617 A1    Jul. 29, 2021

Related U.S. Application Data

(60) Provisional application No. 62/967,388, filed on Jan. 29, 2020.

(51) Int. Cl.
*G16C 10/00* (2019.01)
*G06F 17/14* (2006.01)
(Continued)

(52) U.S. Cl.
CPC .............. *G16C 10/00* (2019.02); *G06F 17/14* (2013.01); *G06F 30/20* (2020.01); *G06N 10/60* (2022.01); *G06F 2111/10* (2020.01)

(58) Field of Classification Search
CPC ........ G16C 10/00; G06N 10/00; G06F 30/20; G06F 17/14; G06F 2111/10
See application file for complete search history.

(56) References Cited

U.S. PATENT DOCUMENTS 8,633,437 B2    1/2014 Dantus et al.
9,335,606 B2    5/2016 Hanson et al.
(Continued)

OTHER PUBLICATIONS

Harris, Sarah A., and Vivien M. Kendon. "Quantum-assisted biomolecular modelling." Philosophical Transactions of the Royal Society A: Mathematical, Physical and Engineering Sciences 368. 1924 (2010): 3581-3592. (Year: 2010).*

(Continued)

*Primary Examiner* — Li B. Zhen
*Assistant Examiner* — Griffin Tanner Bean
(74) *Attorney, Agent, or Firm* — Patterson + Sheridan, LLP

(57) ABSTRACT

A method of performing computation using a hybrid quantum-classical computing system comprising a classical computer and a quantum processor includes computing, by use of a classical computer, short-range inter-particle interaction energies and self-energies of a group of interacting particles, transforming the quantum processor from an initial state to a charge-position encoded state, applying Quantum Fourier transformation to the quantum processor, measuring an estimated amplitude of the Fourier transformed superposition state on the quantum processor, computing long-range inter-particle interaction energies based on the measured estimated amplitude of the Fourier transformed superposition state, and computing and outputting a sum of the short-range inter-particle interaction energies, the self-energies of the system, and the long-range inter-particle interaction energies as a total inter-particle interaction energies of the system.

17 Claims, 7 Drawing Sheets

(51) Int. Cl.
G06F 30/20 (2020.01)
G06N 10/60 (2022.01)
G06F 111/10 (2020.01)

(56) References Cited

U.S. PATENT DOCUMENTS

| | | | |
|---|---|---|---|
| 9,858,531 | B1 | 1/2018 | Monroe et al. |
| 2006/0249670 | A1 | 11/2006 | Monroe et al. |
| 2007/0239366 | A1* | 10/2007 | Hilton .................... B82Y 10/00 703/11 |
| 2009/0213444 | A1 | 8/2009 | Goto et al. |
| 2018/0114138 | A1 | 4/2018 | Monroe et al. |
| 2019/0197426 | A1* | 6/2019 | Kawano .................. G06F 17/14 |
| 2021/0279631 | A1* | 9/2021 | Pichler .................... G06N 10/60 |

OTHER PUBLICATIONS

Choi, Taeyoung, et al. "Optimal quantum control of multimode couplings between trapped ion qubits for scalable entanglement." Physical review letters 112.19 (2014): 190502. (Year: 2014).*

Sagui, Celeste, and Thomas A. Darden. "Molecular dynamics simulations of biomolecules: long-range electrostatic effects." Annual review of biophysics and biomolecular structure 28.1 (1999): 155-179. (Year: 1999).*

International Search Report dated May 29, 2020 for Application No. PCT/US2020/015232.

International Search Report dated May 28, 2020 for Application No. PCT/US2020/015234.

International Search Report dated May 28, 2020 for Application No. PCT/US2020/015235.

Aspuru-Guzik. Alan, Dutoi. Anthony D., Love, P. J., Head-Gordon, M. (2005). Simulated Quantum Computation of Molecular Energies. Science, 309(5741), 1704-1707. https://doi.org/10.1126/science.1113479.

Aloul, F. A., Ramani, A., Markov, I. L., Sakallah, K. A. (2002). Solving Difficult SAT Instances in the Presence of Symmetry. Proceedings of the 39th Annual Design Automation Conference, 731-736. https://doi.org/10.1145/513918.514102.

Babbush, R., Gidney, C., Berry, D. W., Wiebe, N., McClean, J., Paler, A., Fowler, A., Neven, H. (2018). Encoding Electronic Spectra in Quantum Circuits with Linear T Complexity. Physical Review X, 8(4), 041015. https://doi.org/10.1103/PhysRevX.8.041015.

Ballance, C. J., Harty, T. P., Linke, N. M., Sepiol, M. A., Lucas, D. M. (2016). High-Fidelity Quantum Logic Gates Using Trapped-Ion Hyperfine Qubits. Physical Review Letters, 117(6), 060504. https://doi.org/10.1103/PhysRevLett.117.060504.

Barkoutsos, P. K., Gonthier, J. F., Sokolov, I., Moll, N., Salis, G., Fuhrer, A., Ganzhom, M., Egger, D. J., Troyer, M., Mezzacapo, A., Filipp, S., Tavernelli, I. (2018). Quantum algorithms for electronic structure calculations: particle-hole Hamiltonian and optimized wavefunction expansions. Physical Review A, 98(2), 022322. https://doi.org/10.1103/PhysRevA.98.022322.

Beauregard, S. (2003). Circuit for Shor"s algorithm using 2n+3 qubits. Quantum Information and Computation, 3(2), 175-185. https://doi.org/https://dl.acm.org/doi/10.5555/2011517.2011525.

Benedetti, M., Garcia-Pintos, D., Perdomo, O., Leyton-Ortega, V., Nam, Y., Perdomo-Ortiz, A. (2019). A generative modeling approach for benchmarking and training shallow quantum circuits. Npj Quantum Information, 5, 45. https://doi.org/10.1038/s41534-019-0157-8.

Bera, D., Fenner, S., Green, F., Homer, S. (2008). Universal Quantum Circuits. ArXiv:0804.2429 [Cs.CC].

Bernstein, E., Vazirani, U., Comput, S. J. (1997). Quantum Complexity Theory. SIAM Journal on Computing, 26(5), 1411-1473. https://doi.org/10.1137/S0097539796300921.

Blumel, R., Grzesiak, N., Nam, Y. (2019). Power-optimal, stabilized entangling gate between trapped-ion qubits. ArXiV:1905.09292 [Quant-Ph].

Boyd, S. P., Vandenberghe, L. (2004). Convex optimization. Cambridge University Press.

Bravyi, S., Gambetta, J. M., Mezzacapo, A., Temme, K. (2017). Tapering off qubits to simulate fermionic Hamiltonians. ArXiv:1701.08213 [Quant-Ph].

Bravyi, S., Haah, J. (2012). Magic-state distillation with low overhead. Physical Review A, 86(5), 052329. https://doi.org/10.1103/PhysRevA.86.052329.

Bravyi, S. B., Landau, L. D., Kitaev, A. Y. (2002). Fermionic quantum computation. Annals of Physics, 298(1), 210-226. https://doi.org/10.1006/aphy.2002.6254Calderon-Vargas, F. A., Barron, G. S., Deng, X.-H., Sigillito, A. J., Barnes, E., Economou, S. E. (2019). Fast high-fidelity entangling gates for spin qubits in Si double quantum dots. Physical Review B, 100(3), 035304. https://doi.org/10.1103/PhysRevB.100.035304.

Childs, A. M., Maslov, D., Nam, Y., Ross, N. J., Su, Y. (2018). Toward the first quantum simulation with quantum speedup. Proceedings of the National Academy of Sciences of the United States of America, 115(38), 9456-9461. https://doi.org/10.1073/pnas.1801723115.

Choi, T., Debnath, S., Manning, T. A., Figgatt, C., Gong, Z. X., Duan, L. M., Monroe, C. (2014). Optimal quantum control of multimode couplings between trapped ion qubits for scalable entanglement. Physical Review Letters, 112(19), 190502. https://doi.org/10.1103/PhysRevLett.112.190502.

Chow, J. M. (2010). Quantum Information Processing with Superconducting Qubits. Yale University.

Colless, J. I., Ramasesh, V. V., Dahlen, D., Blok, M. S., Kimchi-Schwartz, M. E., McClean, J. R., Carter, J., De Jong, W. A., Siddiqi, I. (2018). Computation of Molecular Spectra on a Quantum Processor with an Error-Resilient Algorithm. Physical Review X, 8(1), 011021. https://doi.org/10.1103/PhysRevX.8.011021.

Cormen, T. H., Leiserson, C. E., Rivest, R. L., Clifford Stein. (2009). Introduction to algorithms. MIT press.

Crooks, G. E. (2018). Performance of the Quantum Approximate Optimization Algorithm on the Maximum Cut Problem. ArXiv:1811.08419 [Quant-Ph].

Debnath, S., Linke, N. M., Figgatt, C., Landsman, K. A., Wright, K., Monroe, C. (2016). Demonstration of a small programmable quantum computer with atomic qubits. Nature, 536(7614), 63-66. https://doi.org/10.1038/nature18648.

Dobsiček, M., Johansson, G., Shumeiko, V., Wendin, G. (2007). Arbitrary accuracy iterative phase estimation algorithm as a two qubit benchmark. Physical Review A, 76(3), 030306. https://doi.org/10.1103/PhysRevA.76.030306.

Draper, T. G., Kutin, S. A., Rains, E. M., Svore, K. M. (2006). A Logarithmic-Depth Quantum Carry-Lookahead Adder. Quantum Information Computation, 6(4), 351-369. https://doi.org/10.5555/2012086.2012090.

Dumitrescu, E. F., McCaskey, A. J., Hagen, G., Jansen, G. R., Morris, T. D., Papenbrock, T., Pooser, R. C., Dean, D. J., Lougovski, P. (2018). Cloud Quantum Computing of an Atomic Nucleus. Physical Review Letters, 120(21), 210501. https://doi.org/10.1103/PhysRevLett.120.210501.

Endo, S., Benjamin, S. C., Li, Y. (2018). Practical Quantum Error Mitigation for Near-Future Applications. Physical Review X, 8(3), 031027. https://doi.org/10.1103/PhysRevX.8.031027.

Endo, S., Jones, T., McArdle, S., Yuan, X., Benjamin, S. (2019). Variational quantum algorithms for discovering Hamiltonian spectra. Physical Review A, 99(6), 062304. https://doi.org/10.1103/PhysRevA.99.062304.

Evenbly, G., Vidal, G. (2007). Algorithms for entanglement renormalization. Physical Review B, 79(14), 144108. https://doi.org/10.1103/PhysRevB.79.144108.

Farhi, E., Goldstone, J., Gutmann, S. (2014). A Quantum Approximate Optimization Algorithm. ArXiv: 1411.4028 [Quant-Ph].

Feynman, R. P. (1982). Simulating Physics with Computers. In International Journal of Theoretical Physics (vol. 21, Issue 6). https://doi.org/10.1007/BF02650179.

Figgatt, C., Ostrander, A., Linke, N. M., Landsman, K. A., Zhu, D., Maslov, D., Monroe, C. (2019). Parallel Entangling Operations on a Universal Ion Trap Quantum Computer. Nature, 572, 368-372. https://doi.org/10.1038/s41586-019-1427-5.

(56) References Cited

OTHER PUBLICATIONS

Figgatt, C. M. (2018). Building and Programming a Universal Ion Trap Quantum Computer. University of Maryland.

Gaebler, J. P., Tan, T. R., Lin, Y., Wan, Y., Bowler, R., Keith, A. C., Glancy, S., Coakley, K., Knill, E., Leibfried, D., Wineland, D. J. (2016). High-Fidelity Universal Gate Set for Be 9 + Ion Qubits. Physical Review Letters, 117(6), 060505. https://doi.org/10.1103/PhysRevLett.117.060505.

Gambetta, J. M., Motzoi, F., Merkel, S. T., Wilhelm, F. K. (2011). Analytic control methods for high-fidelity unitary operations in a weakly nonlinear oscillator. Physical Review A, 83(1), 012308. https://doi.org/10.1103/PhysRevA.83.012308.

Gene M. Amdahl. (1967). Validity of the single processor approach to achieving large scale computing capabilities. AFIPS Spring Joint Computer Conference.

Goemans, E. X., Williamson, D. P., Williamson, D. P., Goemans, M. X. (1994). Improved Approximation Algorithms for Maximum Cut and Satisfiability Problems Using Semidefinite Programming. Journal of the Association for Computing Machinery, 42(6), 1115-1145. https://doi.org/10.1145/227683.227684.

Green, T. J., Biercuk, M. J. (2015). Phase-modulated decoupling and error suppression in qubit-oscillator systems. Physical Review Letters, 114(12), 120502. https://doi.org/10.1103/PhysRevLett.114.120502.

Grover, L. K. (1997). Quantum Mechanics Helps in Searching for a Needle in a Haystack. Physical Review Letters, 79 (2), 325. https://doi.org/https://doi.org/10.1103/PhysRevLett.79.325.

Grzesiak, N., Blumel, R., Wright, K., Beck, K. M., Pisenti, N. C., Li, M., Chaplin, V., Amini, J. M., Debnath, S., Chen, J. S., Nam, Y. (2020). Efficient arbitrary simultaneously entangling gates on a trapped-ion quantum computer. Nature Communications, 11, 2963. https://doi.org/10.1038/s41467-020-16790-9.

Hadfield, S., Papageorgiou, A. (2018). Divide and conquer approach to quantum Hamiltonian simulation. New Journal of Physics, 20(4), 043003. https://doi.org/10.1088/1367-2630/aab1ef.

Harrow, A. W., Hassidim, A., Lloyd, S. (2009). Quantum algorithm for linear systems of equations. Physical Review Letters, 103(15), 150502. https://doi.org/10.1103/PhysRevLett.103.150502.

Harty, T. P., Allcock, D. T. C., Ballance, C. J., Guidoni, L., Janacek, H. A., Linke, N. M., Stacey, D. N., Lucas, D. M. (2014). High-fidelity preparation, gates, memory, and readout of a trapped-ion quantum bit. Physical Review Letters, 113(22), 220501. https://doi.org/10.1103/PhysRevLett.113.220501.

Hempel, C., Maier, C., Romero, J., McClean, J., Monz, T., Shen, H., Jurcevic, P., Lanyon, B., Love, P., Babbush, R., Aspuru-Guzik, A., Blatt, R., Roos, C. (2018). Quantum chemistry calculations on a trapped-ion quantum simulator. Physical Review X, 8(3), 031022. https://doi.org/10.1103/PhysRevX.8.031022.

Hewitt, E., Hewitt, R. E. (1979). The Gibbs-Wilbraham Phenomenon: An Episode in Fourier Analysis. Archive for History of Exact Sciences, 21, 129-160. https://doi.org/10.1007/BF00330404.

Higgott, O., Wang, D., Brierley, S. (2019). Variational Quantum Computation of Excited States. Quantum, 156. https://doi.org/10.22331/q-2019-07-01-156.

Jones, N. C., Whitfield, J. D., McMahon, P. L., Yung, M. H., Meter, R. Van, Aspuru-Guzik, A., Yamamoto, Y. (2012). Faster quantum chemistry simulation on fault-tolerant quantum computers. New Journal of Physics, 14, 115023. https://doi.org/10.1088/1367-2630/14/11/115023.

Kandala, A., Mezzacapo, A., Temme, K., Takita, M., Brink, M., Chow, J. M., Gambetta, J. M. (2017). Hardware-efficient Variational Quantum Eigensolver for Small Molecules and Quantum Magnets. Nature, 549, 242-246. https://doi.org/10.1038/nature23879.

Kassal, I., Jordan, S. P., Love, P. J., Mohseni, M., Aspuru-Guzik, A. (2008). Polynomial-time quantum algorithm for the simulation of chemical dynamics. Proceedings of the National Academy of Sciences of the United States of America, 105(48), 18681-18686. https://doi.org/10.1073/pnas.0808245105.

Kim, I. H. (2017). Noise-resilient preparation of quantum many-body ground states. ArXiv:1703.00032 [Quant-Ph].

Kim, I. H., Swingle, B. (2017). Robust entanglement renormalization on a noisy quantum computer. ArXiv:1711.07500 [Quant-Ph].

Kitaev, A. Y., Landau, L. D. (1995). Quantum measurements and the Abelian Stabilizer Problem. ArXiv:Quant-Ph/9511026.

Klco, N., Dumitrescu, E. F., McCaskey, A. J., Morris, T. D., Pooser, R. C., Sanz, M., Solano, E., Lougovski, P., Savage, M. J. (2018). Quantum-Classical Computation of Schwinger Model Dynamics using Quantum Computers. Physical Review A, 98(3), 032331. https://doi.org/10.1103/PhysRevA.98.032331.

Landsman, K. A., Figgatt, C., Schuster, T., Linke, N. M., Yoshida, B., Yao, N. Y., Monroe, C. (2019). Verified Quantum Information Scrambling. Nature, 567(7746), 61-65. https://doi.org/10.1038/s41586-019-0952-6.

Leung, P. H., Brown, K. R. (2018). Entangling an arbitrary pair of qubits in a long ion crystal. Physical Review A, 98(3), 032318. https://doi.org/10.1103/PhysRevA.98.032318.

Leung, P. H., Landsman, K. A., Figgatt, C., Linke, N. M., Monroe, C., Brown, K. R. (2018). Robust 2-Qubit Gates in a Linear Ion Crystal Using a Frequency-Modulated Driving Force. Physical Review Letters, 120(2), 020501. https://doi.org/10.1103/PhysRevLett.120.020501.

Lin, G.-D., Zhu, S.-L., Islam, R., Kim, K., Chang, M.-S., Korenblit, S., Monroe, C., Duan, L.-M. (2009). Large-scale quantum computation in an anharmonic linear ion trap. Europhysics Letters, 86(6), 60004. https://doi.org/10.1209/0295-5075/86/60004.

Linke, N. M., Maslov, D., Roetteler, M., Debnath, S., Figgatt, C., Landsman, K. A., Wright, K., Monroe, C. (2017). Experimental comparison of two quantum computing architectures. Proceedings of the National Academy of Sciences of the United States of America, 114(13), 3305-3310. https://doi.org/10.1073/pnas.1618020114.

Liu, J.-G., Zhang, Y.-H., Wan, Y., Wang, L. (2019). Variational quantum eigensolver with fewer qubits. Physical Review Research, 1(2), 023025. https://doi.org/10.1103/physrevresearch.1.023025.

Lloyd, S., Mohseni, M., Rebentrost, P. (2014). Quantum principal component analysis. Nature Physics, 10(9), 631-633. https://doi.org/10.1038/NPHYS3029.

Lu, Y., Zhang, S., Zhang, K., Chen, W., Shen, Y., Zhang, J., Zhang, J.-N., Kim, K. (2019). Scalable global entangling gates on arbitrary ion qubits. Nature, 572, 363-367. https://doi.org/10.1038/s41586-019-1428-4.

Lu, D., Xu, N., Xu, R., Chen, H., Gong, J., Peng, X., Du, J. (2011). Simulation of chemical isomerization reaction dynamics on a NMR quantum simulator. Physical Review Letters, 107(2), 020501. https://doi.org/10.1103/PhysRevLett.107.020501.

MacDonald, J. K. L. (1934). On the Modified Ritz Variation Method. Physical Review, 46(9), 828. https://doi.org/10.1103/PhysRev.46.828.

Marquet, C., Schmidt-Kaler, F., James, D. F. V. (2003). Phonon-phonon interactions due to non-linear effects in a linear ion trap. Applied Physics B, 76(3), 199-208. https://doi.org/10.1007/s00340-003-1097-7.

Maslov, D. (2017). Basic circuit compilation techniques for an ion-trap quantum machine. New Journal of Physics, 19(2), 023035. https://doi.org/10.1088/1367-2630/aa5e47.

Maslov, D. (2016). Advantages of using relative-phase Toffoli gates with an application to multiple control Toffoli optimization. Physical Review A, 93(2), 022311. https://doi.org/10.1103/PhysRevA.93.022311.

Maslov, D., Nam, Y. (2018). Use of global interactions in efficient quantum circuit constructions. New Journal of Physics, 20(3), 033018. https://doi.org/10.1088/1367-2630/aaa398.

Maslov, D., Nam, Y., Kim, J. (2019). An Outlook for Quantum Computing [Point of View]. Proceedings of the IEEE, 107(1), 5-10. https://doi.org/10.1109/JPROC.2018.2884353.

McArdle, S., Endo, S., Aspuru-Guzik, A., Benjamin, S., Yuan, X. (2020). Quantum computational chemistry. Reviews of Modern Physics, 92(1), 015003. https://doi.org/10.1103/RevModPhys.92.015003.

McArdle, S., Yuan, X., Benjamin, S. (2019). Error-mitigated digital quantum simulation. Physical Review Letters, 122(18), 180501. https://doi.org/10.1103/PhysRevLett.122.180501.

(56) References Cited

OTHER PUBLICATIONS

McClean, J. R., Boixo, S., Smelyanskiy, V. N., Babbush, R., Neven, H. (2018). Barren plateaus in quantum neural network training landscapes. Nature Communications, 9, 4812. https://doi.org/10.1038/s41467-018-07090-4.

McClean, J. R., Romero, J., Babbush, R., Aspuru-Guzik, A. (2016). The theory of variational hybrid quantum-classical algorithms. New Journal of Physics, 18(2), 023023. https://doi.org/10.1088/1367-2630/18/2/023023.

McClean, J. R., Schwartz, M. E., Carter, J., de Jong, W. A. (2017). Hybrid Quantum-Classical Hierarchy for Mitigation of Decoherence and Determination of Excited States. Physical Review A, 95(4), 042308. https://doi.org/10.1103/PhysRevA.95.042308.

Merrill, J. T., Brown, K. R. (2014). Progress in compensating pulse sequences for quantum computation. In Sabre Kais (Ed.), Quantum Information and Computation for Chemistry (pp. 241-294). John Wiley Sons. https://doi.org/10.1002/9781118742631.ch10.

Moll, N., Fuhrer, A., Staar, P., Tavernelli, I. (2016). Optimizing qubit resources for quantum chemistry simulations in second quantization on a quantum computer. Journal of Physics A: Mathematical and Theoretical, 49(29), 295301. https://doi.org/10.1088/1751-8113/49/29/295301.

Mølmer, K., Sørensen, A. (1999). Multiparticle Entanglement of Hot Trapped Ions. Physical Review Letters, 82(9), 1835. https://doi.org/10.1103/PhysRevLett.82.1835.

Muller, M. M., Haakh, H. R., Calarco, T., Koch, C. P., Henkel, C. (2011). Prospects for fast Rydberg gates on an atom chip. Quantum Information Processing, 10(6), 771-792. https://doi.org/10.1007/s11128-011-0296-0.

Nam, Y., Chen, J. S., Pisenti, N. C., Wright, K., Delaney, C., Maslov, D., Brown, K. R., Allen, S., Amini, J. M., Apisdorf, J., Beck, K. M., Blinov, A., Chaplin, V., Chmielewski, M., Collins, C., Debnath, S., Hudek, K. M., Ducore, A. M., Keesan, M., Kim, J. (2020). Ground-state energy estimation of the water molecule on a trapped-ion quantum computer. Npj Quantum Information, 6, 33. https://doi.org/10.1038/s41534-020-0259-3.

Nam, Y., Maslov, D. (2019). Low-cost quantum circuits for classically intractable instances of the Hamiltonian dynamics simulation problem. Npj Quantum Information, 5, 44. https://doi.org/10.1038/s41534-019-0152-0.

Nam, Y., Su, Y., Maslov, D. (2020). Approximate quantum Fourier transform with O(n log(n)) T gates. Npj Quantum Information, 6, 26. https://doi.org/10.1038/s41534-020-0257-5.

Nielsen, M. A., Chuang, I. L. (2010). Quantum computation and quantum information. Cambridge University Press. https://doi.org/10.1017/CBO9780511976667.

O"Gorman, J., Campbell, E. T. (2017). Quantum computation with realistic magic-state factories. Physical Review A, 95(3), 032338. https://doi.org/10.1103/PhysRevA.95.032338.

O"Malley, P. J. J., Babbush, R., Kivlichan, I. D., Romero, J., McClean, J. R., Barends, R., Kelly, J., Roushan, P., Tranter, A., Ding, N., Campbell, B., Chen, Y., Chen, Z., Chiaro, B., Dunsworth, A., Fowler, A. G., Jeffrey, E., Megrant, A., Mutus, J. Y., Martinis, J. M. (2016). Scalable Quantum Simulation of Molecular Energies. Physical Review X, 6(3), 031007. https://doi.org/10.1103/PhysRevX.6.031007.

Orus, R., Mugel, S., Lizaso, E. (2019). Quantum computing for finance: overview and prospects. Reviews in Physics, 4, 100028. https://doi.org/10.1016/j.revip.2019.100028.

Peruzzo, A., McClean, J., Shadbolt, P., Yung, M. H., Zhou, X. Q., Love, P. J., Aspuru-Guzik, A., O"Brien, J. L. (2014). A variational eigenvalue solver on a photonic quantum processor. Nature Communications, 5, 4213. https://doi.org/10.1038/ncomms5213.

Preskill, J. (2018). Quantum Computing in the NISQ era and beyond. Quantum, 2, 79. https://doi.org/10.22331/q-2018-08-06-79.

Reiher, M., Wiebe, N., Svore, K. M., Wecker, D., Troyer, M. (2017). Elucidating reaction mechanisms on quantum computers. Proceedings of the National Academy of Sciences of the United States of America, 114(29), 7555-7560. https://doi.org/10.1073/pnas.1619152114.

Santagati, R., Wang, J., Gentile, A. A., Paesani, S., Wiebe, N., Mcclean, J. R., Morley-Short, S., Shadbolt, P. J., Bonneau, D., Silverstone, J. W., Tew, D. P., Zhou, X., O"brien, J. L., Thompson, M. G. (2018). Witnessing eigenstates for quantum simulation of Hamiltonian spectra. Science Advances, 4(1), eaap9646. https://doi.org/10.1126/sciadv.aap9646.

Seeley, J. T., Richard, M. J., Love, P. J. (2012). The Bravyi-Kitaev transformation for quantum computation of electronic structure. Journal of Chemical Physics, 137(22), 224109. https://doi.org/10.1063/1.4768229.

Shantanu, D. (2016). A Programmable Five Qubit Quantum Computer Using Trapped Atomic Ions. University of Maryland Department of Physics and National Institute of Standards and Technology.

Shen, Y., Zhang, X., Zhang, S., Zhang, J. N., Yung, M. H., Kim, K. (2017). Quantum implementation of the unitary coupled cluster for simulating molecular electronic structure. Physical Review A, 95(2). https://doi.org/10.1103/PhysRevA.95.020501.

Shehab, O., Landsman, K. A., Nam, Y., Zhu, D., Linke, N. M., Keesan, M. J., Pooser, R. C., Monroe, C. R. (2019). Toward convergence of effective field theory simulations on digital quantum computers. Physical Review A, 100(6), 062319. https://doi.org/10.1103/PhysRevA.100.062319.

Shor, P. W. (1999). Polynomial-Time Algorithms for Prime Factorization and Discrete Logarithms on a Quantum Compuer. SIAM Review, 41(2), 303-332.

Shende, V. V., Markov, I. L., Bullock, S. S. (2004). Minimal universal two-qubit controlled-NOT-based circuits. Physical Review A, 69(6), 062321. https://doi.org/10.1103/PhysRevA.69.062321.

Sørensen, A., Mølmer, K. (1999). Quantum Computation with Ions in Thermal Motion. Physical Review Letters, 82(9), 1971. https://doi.org/10.1103/PhysRevLett.82.1971.

Sporl, A., Schulte-Herbruggen, T., Glaser, S. J., Bergholm, V., Storcz, M. J., Ferber, J., Wilhelm, F. K. (2007). Optimal control of coupled Josephson qubits. Physical Review A, 75(1), 012302. https://doi.org/10.1103/PhysRevA.75.012302.

Takeshita, T., Rubin, N. C., Jiang, Z., Lee, E., Babbush, R., McClean, J. R. (2020). Increasing the representation accuracy of quantum simulations of chemistry without extra quantum resources. Physical Review X, 10(1), 011004. https://doi.org/10.1103/PhysRevX.10.011004.

Toloui, B., Love, P. J. (2013). Quantum Algorithms for Quantum Chemistry based on the sparsity of the CI-matrix. ArXiv:1312.2579 [Quant-Ph].

Tranter, A., Sofia, S., Seeley, J., Kaicher, M., McClean, J., Babbush, R., Coveney, P. V., Mintert, F., Wilhelm, F., Love, P. J. (2015). The Bravyi-Kitaev transformation: Properties and applications. International Journal of Quantum Chemistry, 115(19), 1431-1441. https://doi.org/10.1002/qua.24969.

Van Dam, W., Hallgren, S., Ip, L. (2006). Quantum algorithms for some hidden shift problems. SIAM Journal on Computing, 36(3), 763-778. https://doi.org/10.1137/S009753970343141X.

Wang, Y., Um, M., Zhang, J., An, S., Lyu, M., Zhang, J. N., Duan, L. M., Yum, D., Kim, K. (2017). Single-qubit quantum memory exceeding ten-minute coherence time. Nature Photonics, 11(10), 646-650. https://doi.org/10.1038/s41566-017-0007-1.

Ward, N. J., Kassal, I., Aspuru-Guzik, A. (2009). Preparation of many-body states for quantum simulation. Journal of Chemical Physics, 130(19), 194105. https://doi.org/10.1063/1.3115177.

Webb, A. E., Webster, S. C., Collingbourne, S., Bretaud, D., Lawrence, A. M., Weidt, S., Mintert, F., Hensinger, W. K. (2018). Resilient entanglement gates for trapped ions. Physical Review Letters, 121(18), 180501. https://doi.org/10.1103/PhysRevLett.121.180501.

Wecker, D., Bauer, B., Clark, B. K., Hastings, M. B., Troyer, M. (2014). Gate count estimates for performing quantum chemistry on small quantum computers. Physical Review A, 90(2), 022305. https://doi.org/10.1103/PhysRevA.90.022305.

Weinstein, D. H. (1934). Modified Ritz Method. Proceedings of the National Academy of Sciences, 20, 529-532.

Welch, J., Greenbaum, D., Mostame, S., Aspuru-Guzik, A. (2014). Efficient quantum circuits for diagonal unitaries without ancillas. New Journal of Physics, 16, 033040. https://doi.org/10.1088/1367-2630/16/3/033040.

(56) References Cited

OTHER PUBLICATIONS

Whitfield, J. D., Biamonte, J., Aspuru-Guzik, A. (2011). Simulation of electronic structure Hamiltonians using quantum computers. Molecular Physics, 109(5), 735-750. https://doi.org/10.1080/00268976.2011.552441.

Wineland, D. J., Monroe, C., Itano, W. M., Leibfried, D., King, B. E., Meekhof, D. M. (1998). Experimental Issues in Coherent Quantum-State Manipulation of Trapped Atomic Ions. Journal of Research of the National Institute of Standards and Technology, 103(3), 259. https://doi.org/10.6028/jres.103.019.

Wright, K., Beck, K. M., Debnath, S., Amini, J. M., Nam, Y., Grzesiak, N., Chen, J. S., Pisenti, N. C., Chmielewski, M., Collins, C., Hudek, K. M., Mizrahi, J., Wong-Campos, J. D., Allen, S., Apisdorf, J., Solomon, P., Williams, M., Ducore, A. M., Blinov, A., Kim, J. (2019). Benchmarking an 11-qubit quantum computer. Nature Communications, 10, 5464. https://doi.org/10.1038/s41467-019-13534-2.

Wu, Y., Wang, S. T., Duan, L.-M. (2018). Noise analysis for high-fidelity quantum entangling gates in an anharmonic linear Paul trap. Physical Review A, 97(6), 062325. https://doi.org/10.1103/PhysRevA.97.062325.

Zhu, S. L., Monroe, C., Duan, L. M. (2006). Arbitrary-speed quantum gates within large ion crystals through minimum control of laser beams. Europhysics Letters, 73, 485-491. https://doi.org/10.1209/epl/i2005-10424-4.

Zhu, S.-L., Monroe, C., Duan, L.-M. (2006). Trapped ion quantum computation with transverse phonon modes. Physical Review Letters, 97(5), 050505. https://doi.org/10.1103/PhysRevLett.97.050505.

Balbuena, P. B., Johnston, K. P., & Rossky, P. J. (1996). Molecular Dynamics Simulation of Electrolyte Solutions in Ambient and Supercritical Water. 1. Ion Solvation. The Journal of Physical Chemistry, 100(7). https://doi.org/10.1021/jp952194o.

Brodholt, J. P. (1998). Molecular dynamics simulations of aqueous NaCl solutions at high pressures and temperatures. Chemical Geology, 151(1-4). https://doi.org/10.1016/S0009-2541(98)00066-7.

Cooley, J. W., & Tukey, J. W. (1965). An algorithm for the machine calculation of complex Fourier series. Mathematics of Computation, 19(90). https://doi.org/10.1090/S0025-5718-1965-0178586-1.

Kohlmeyer, A., & Vermaas, J. (2017). akohlmey/topotools: Release 1.7. http://dx.doi.org/10.5281/zenodo.545655.

Kremer, K., Robbins, M. O., & Grest, G. S. (1986). Phase Diagram of Yukawa Systems: Model for Charge-Stabilized Colloids. Physical Review Letters, 57(21). https://doi.org/10.1103/PhysRevLett.57.2694.

Quane, D. (1970). Crystal lattice energy and the Madelung constant. Journal of Chemical Education, 47(5). https://doi.org/10.1021/ed047p396.

\* cited by examiner

ACCELERATED MOLECULAR DYNAMICS SIMULATION METHOD ON A QUANTUM-CLASSICAL HYBRID COMPUTING SYSTEM

CROSS-REFERENCE TO RELATED APPLICATIONS

This application claims the benefit to U.S. Provisional Application No. 62/967,388, filed Jan. 29, 2020, which is incorporated by reference herein.

BACKGROUND

Field

The present disclosure generally relates to a method of performing computations in a hybrid computing system, and more specifically, to a method of obtaining energies of a physical system having interacting particles by molecular dynamics (MD) simulations performed in a hybrid computing system that includes a classical computer and quantum computer, where the quantum computer operates based on a group of trapped ions and the hybrid computing system can be referred to as a hybrid quantum-classical computing system.

Description of the Related Art

In quantum computing, quantum bits or qubits, which are analogous to bits representing a "0" and a "1" in a classical (digital) computer, are required to be prepared, manipulated, and measured (read-out) with near perfect control during a computation or computation process. Imperfect control of the qubits leads to errors that can accumulate over the computation process, limiting the size of a quantum computer that can perform reliable computations.

Among the types of physical systems or qubit technologies upon which it is proposed to build large-scale quantum computers, is a group of ions (e.g., charged atoms), which are trapped and suspended in vacuum by electromagnetic fields. The ions have internal hyperfine states which are separated by frequencies in the several GHz range and can be used as the computational states of a qubit (referred to as "qubit states"). These hyperfine states can be controlled using radiation provided from a laser, or sometimes referred to herein as the interaction with laser beams. The ions can be cooled to near their motional ground states using such laser interactions. The ions can also be optically pumped to one of the two hyperfine states with high accuracy (preparation of qubits), manipulated between the two hyperfine states (single-qubit gate operations) by laser beams, and their internal hyperfine states detected by fluorescence upon application of a resonant laser beam (read-out of qubits). A pair of ions can be controllably entangled (two-qubit gate operations) by qubit-state dependent force using laser pulses that couple the ions to the collective motional modes of a group of trapped ions, which arise from their Coulombic interaction between the ions. In general, entanglement occurs when pairs or groups of ions (or particles) are generated, interact, or share spatial proximity in ways such that the quantum state of each ion cannot be described independently of the quantum state of the others, even when the ions are separated by a large distance. Other types of physical systems or qubit technologies include the use of super Quantum computers have been shown to improve the performance of certain computational tasks when compared to what classical computers can do, including in different types of physical simulations. In molecular dynamics (MD) simulations, inter-particle interaction energies, including long-range interactions, are calculated. This leads to an increase in the computational complexity as $\mathcal{O}(N^2)$ as the number of interacting particle N increases. Even when an efficient method is used, such as the Ewald summation method, calculating the long-range interactions scales as $\mathcal{O}(N^{3/2})$. The Ewald summation method involves Fourier transformation, which can be sped up by use of a quantum computer.

Therefore, there is a need for methods to speed up MD simulations and quantum computing can be used to speed up the Fourier transformations of already efficient methods such as the Ewald summation method.

SUMMARY

Embodiments of the present disclosure provide a method of performing computation using a hybrid quantum-classical computing system comprising a classical computer and a quantum processor. The method includes computing, by use of a classical computer, short-range inter-particle interaction energies and self-energies of a group of interacting particles, transforming the quantum processor from an initial state to a charge-position encoded state, applying Quantum Fourier transformation to the quantum processor, measuring an estimated amplitude of the Fourier transformed superposition state on the quantum processor, computing long-range inter-particle interaction energies based on the measured estimated amplitude of the Fourier transformed superposition state, and computing and outputting a sum of the short-range inter-particle interaction energies, the self-energies of the system, and the long-range inter-particle interaction energies as a total inter-particle interaction energies of the system.

Embodiments of the present disclosure also provide a hybrid quantum-classical computing system. The hybrid quantum-classical computing system includes a quantum processor comprising a group of trapped ions, each trapped ion of the group of trapped ions having two hyperfine states defining a qubit, one or more lasers configured to emit a laser beam, which is provided to trapped ions in the quantum processor, a classical computer configured to compute short-range inter-particle interaction energies and self-energies of a group of interacting particles, and a system controller configured to transform the quantum processor from an initial state to a charge-position encoded state, transform the quantum processor from the charge-position encoded state to a Fourier transformed superposition state, measure an estimated amplitude of the Fourier transformed superposition state on the quantum processor. The classical computer is further configured to compute long-range inter-particle interaction energies based on the measured estimated amplitude of the Fourier transformed superposition state, compute a sum of the short-range inter-particle interaction energies, the self-energies of the group of the interacting particles, and the long-range inter-particle interaction energies, and output the computed sum of the short-range inter-particle interaction energies, the self-energies of the group of the interacting particles, and the long-range inter-particle interaction energies as a total inter-particle interaction energies of the group of the interacting particles.

Embodiments of the present disclosure further provide a hybrid quantum-classical computing system comprising non-volatile memory having a number of instructions stored therein. The number of instructions, when executed by one or more processors, causes the hybrid quantum-classical computing system to perform operations including computing, by use of the classical computer, short-range inter-particle interaction energies and self-energies of a group of interacting particles, transforming a quantum processor from an initial state to a charge-position encoded state, transforming the quantum processor from the charge-position encoded state to a Fourier transformed superposition state, measuring an estimated amplitude of the Fourier transformed superposition state on the quantum processor, computing, by use of the classical computer, long-range inter-particle interaction energies based on the measured estimated amplitude of the Fourier transformed superposition state, computing, by use of the classical computer, a sum of the short-range inter-particle interaction energies, the self-energies of the group of the interacting particles, and the long-range inter-particle interaction energies, and outputting, by use of the classical computer, the computed sum of the short-range inter-particle interaction energies, the self-energies of the group of the interacting particles, and the long-range inter-particle interaction energies as a total inter-particle interaction energies of the group of the interacting particles.

Embodiments of the present disclosure further provide a method of performing computations using a hybrid quantum-classical computing system comprising a classical computer and a quantum processor. The method includes identifying, by use of the classical computer, a molecular dynamics system to be simulated, computing, by use of the classical computer, multiple energies associated with particles of the molecular dynamics system as part of the simulation, the computing of the multiple energies being based on an Ewald summation method, the computing of the multiple energies including partially offloading the computing of the multiple energies that are based on Fourier transformations to the quantum processor, and determining, by use of the classical computer, a physical behavior of the molecular dynamics system from the computed energies.

Embodiments of the present disclosure further provide a hybrid quantum-classical computing system. The hybrid quantum-classical computing system includes a quantum processor comprising a group of trapped ions, each trapped ion of the group of trapped ions having two hyperfine states defining a qubit, one or more lasers configured to emit a laser beam, which is provided to trapped ions in the quantum processor, a classical computer configured to identify a molecular dynamics system to be simulated, compute multiple energies associated with particles of the molecular dynamics system as part of the simulation, the computing of the multiple energies being based on an Ewald summation method, the computing of the multiple energies including partially offloading the computing of the multiple energies that are based on Fourier transformations to the quantum processor, and determine a physical behavior of the molecular dynamics system from the computed energies, and a system controller configured to control operations on the one or more lasers.

Embodiments of the present disclosure further provide a hybrid quantum-classical computing system comprising non-volatile memory having a number of instructions stored therein. The number of instructions, when executed by one or more processors, causes the hybrid quantum-classical computing system to perform operations including identifying, by use of the classical computer, a molecular dynamics system to be simulated, computing, by use of the classical computer, multiple energies associated with particles of the molecular dynamics system as part of the simulation, the computing of the multiple energies being based on an Ewald summation method, the computing of the multiple energies including partially offloading the computing of the multiple energies that are based on Fourier transformations to the quantum processor, and determining, by use of the classical computer, a physical behavior of the molecular dynamics system from the computed energies, identifying, by use of the classical computer, a molecular dynamics system to be simulated, computing, by use of the classical computer, multiple energies associated with particles of the molecular dynamics system as part of the simulation, the computing of the multiple energies being based on an Ewald summation method, the computing of the multiple energies including partially offloading the computing of the multiple energies that are based on Fourier transformations to the quantum processor, and determining, by use of the classical computer, a physical behavior of the molecular dynamics system from the computed energies.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

Figure 1:
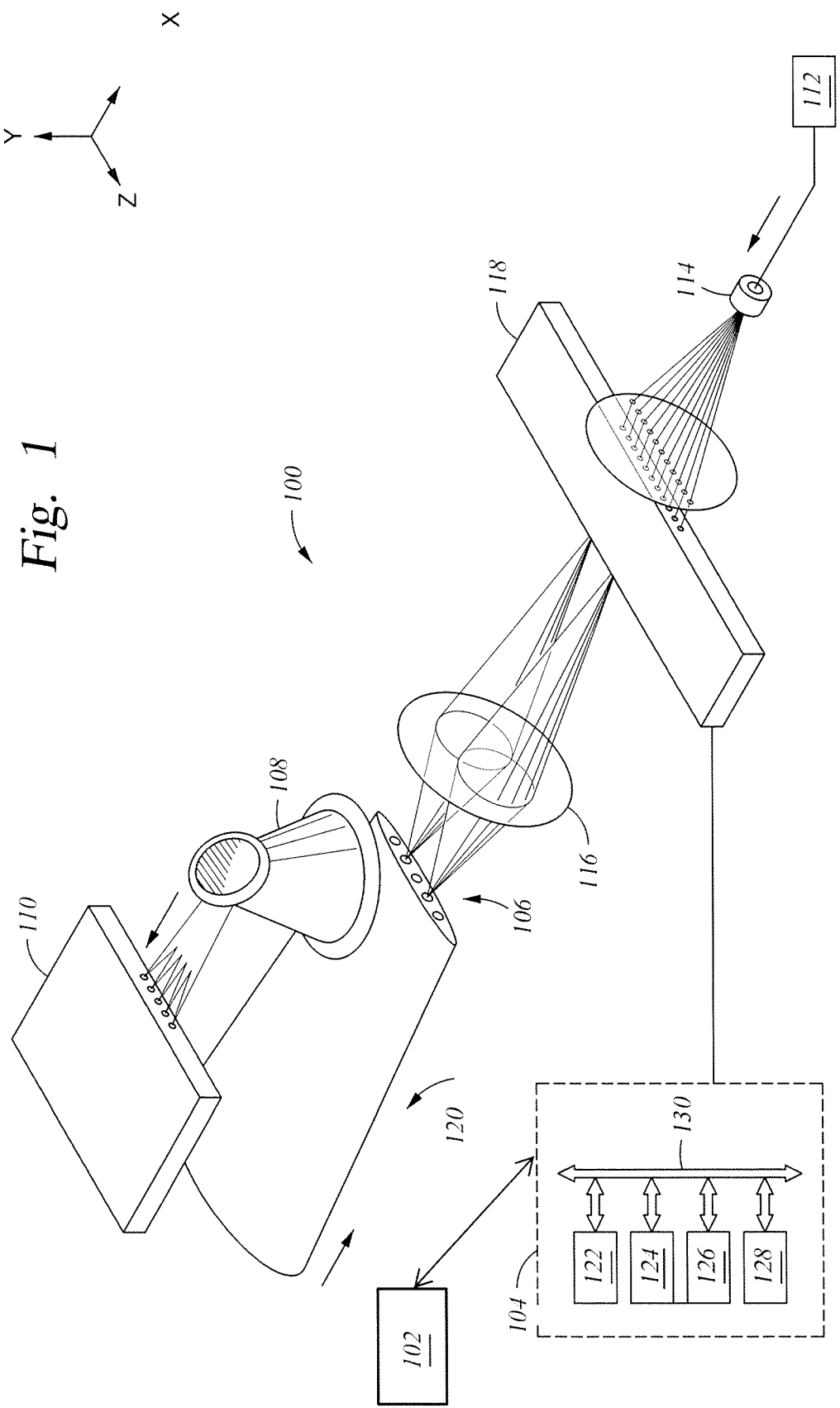
FIG. 1 is a schematic partial view of an ion trap quantum computing system according to one embodiment.

To facilitate understanding, identical reference numerals have been used, where possible, to designate identical elements that are common to the figures. In the figures and the following description, an orthogonal coordinate system including an X-axis, a Y-axis, and a Z-axis is used. The directions represented by the arrows in the drawing are assumed to be positive directions for convenience. It is contemplated that elements disclosed in some embodiments may be beneficially utilized on other implementations without specific recitation.

DETAILED DESCRIPTION

Embodiments described herein are generally related to a method of performing computation in a hybrid computing system, and more specifically, to a method of obtaining energies of a physical system having interacting particles by molecular dynamics (MD) simulations performed in a hybrid computing system that includes a classical computer and quantum computer, where the quantum computer operates based on a group of trapped ions and the hybrid computing system can be referred to as a hybrid quantum-classical computing system.

A hybrid quantum-classical computing system that is able to obtain energies of a physical system having interacting particles by molecular dynamics (MD) simulations may include a classical computer, a system controller, and a quantum processor. As used herein, the terms "quantum computer" and "quantum processor" may be used interchangeably to refer to the hardware/software components that perform a quantum computation. The classical computer performs supporting and system control tasks including selecting a group of interacting particles to be simulated by use of a user interface, computing a part of the energies of the physical system, applying a series of logic gates into laser pulses on the quantum processor and performing measurements by the system controller to estimate the remaining part of the energies of the system, and totaling the energies of the system by use of the classical computer. A software program for performing the tasks is stored in a non-volatile memory within the classical computer.

The quantum processor can be made from different qubit technologies. In one example, for ion trap technologies, the quantum processor includes trapped ions that are coupled with various hardware, including lasers to manipulate internal hyperfine states (qubit states) of the trapped ions and photomultiplier tubes (PMTs), or other type of imaging devices, to read-out the internal hyperfine states (qubit states) of the trapped ions. The system controller receives from the classical computer instructions for controlling the quantum processor, and controls various hardware associated with controlling any and all aspects used to run the instructions for controlling the quantum processor. The system controller also returns a read-out of the quantum processor and thus output of results of the computation(s) performed by the quantum processor to the classical computer.

The methods and systems described herein include an efficient computer simulation routine executed by the quantum processor, within a hybrid quantum-classical computing system, to perform computer simulation of a complex system, such as complex physical systems including but not limited to molecular dynamics. The methods described herein include improvements over conventional computer simulation methods.

General Hardware Configurations

FIG. 1 is a schematic partial view of an ion trap quantum computing system 100, or simply the system 100, according to one embodiment. The system 100 can be representative of a hybrid quantum-classical computing system. The system 100 includes a classical (digital) computer 102 and a system controller 104. Other components of the system 100 shown in FIG. 1 are associated with a quantum processor, including a group 106 of trapped ions (i.e., five shown as circles about equally spaced from each other) that extend along the Z-axis. Each ion in the group 106 of trapped ions is an ion having a nuclear spin I and an electron spin S such that a difference between the nuclear spin I and the electron spin S is zero, such as a positive ytterbium ion, $^{171}Yb^+$, a positive barium ion $^{133}Ba^+$, a positive cadmium ion $^{111}Cd^+$ or $^{113}Cd^+$, which all have a nuclear spin $$I = \frac{1}{2}$$

and the $^2S_{1/2}$ hyperfine states. In some embodiments, all ions in the group 106 of trapped ions are the same species and isotope (e.g., $^{171}Yb^+$). In some other embodiments, the group 106 of trapped ions includes one or more species or isotopes (e.g., some ions are $^{171}Yb^+$ and some other ions are $^{133}Ba^+$). In yet additional embodiments, the group 106 of trapped ions may include various isotopes of the same species (e.g., different isotopes of Yb, different isotopes of Ba). The ions in the group 106 of trapped ions are individually addressed with separate laser beams. The classical computer 102 includes a central processing unit (CPU), memory, and support circuits (or I/O) (not shown). The memory is connected to the CPU, and may be one or more of a readily available memory, such as a read-only memory (ROM), a random access memory (RAM), floppy disk, hard disk, or any other form of digital storage, local or remote. Software instructions, algorithms and data can be coded and stored within the memory for instructing the CPU. The support circuits (not shown) are also connected to the CPU for supporting the processor in a conventional manner. The support circuits may include conventional cache, power supplies, clock circuits, input/output circuitry, subsystems, and the like.

An imaging objective 108, such as an objective lens with a numerical aperture (NA), for example, of 0.37, collects fluorescence along the Y-axis from the ions and maps each ion onto a multi-channel photo-multiplier tube (PMT) 110 (or some other imaging device) for measurement of individual ions. Raman laser beams from a laser 112, which are provided along the X-axis, perform operations on the ions. A diffractive beam splitter 114 creates an array of Raman laser beams 116 that are individually switched using a multi-channel acousto-optic modulator (AOM) 118. The AOM 118 is configured to selectively act on individual ions by individually controlling emission of the Raman laser beams 116. A global Raman laser beam 120, which is non-copropagating to the Raman laser beams 116, illuminates all ions at once from a different direction. In some embodiments, rather than a single global Raman laser beam 120, individual Raman laser beams (not shown) can be used to each illuminate individual ions. The system controller (also referred to as a "RF controller") 104 controls the AOM 118 and thus controls intensities, timings, and phases of laser pulses to be applied to trapped ions in the group 106 of trapped ions. The CPU 122 is a processor of the system controller 104. The ROM 124 stores various programs and the RAM 126 is the working memory for various programs and data. The storage unit 128 includes a nonvolatile memory, such as a hard disk drive (HDD) or a flash memory, and stores various programs even if power is turned off. The CPU 122, the ROM 124, the RAM 126, and the storage unit 128 are interconnected via a bus 130. The system controller 104 executes a control program which is stored in the ROM 124 or the storage unit 128 and uses the RAM 126 as a working area. The control program will include software applications that include program code that may be executed by the CPU 122 in order to perform various functionalities associated with receiving and analyzing data and controlling any and all aspects of the methods and hardware used to implement and operate the ion trap quantum computing system 100 discussed herein.

Figure 2:
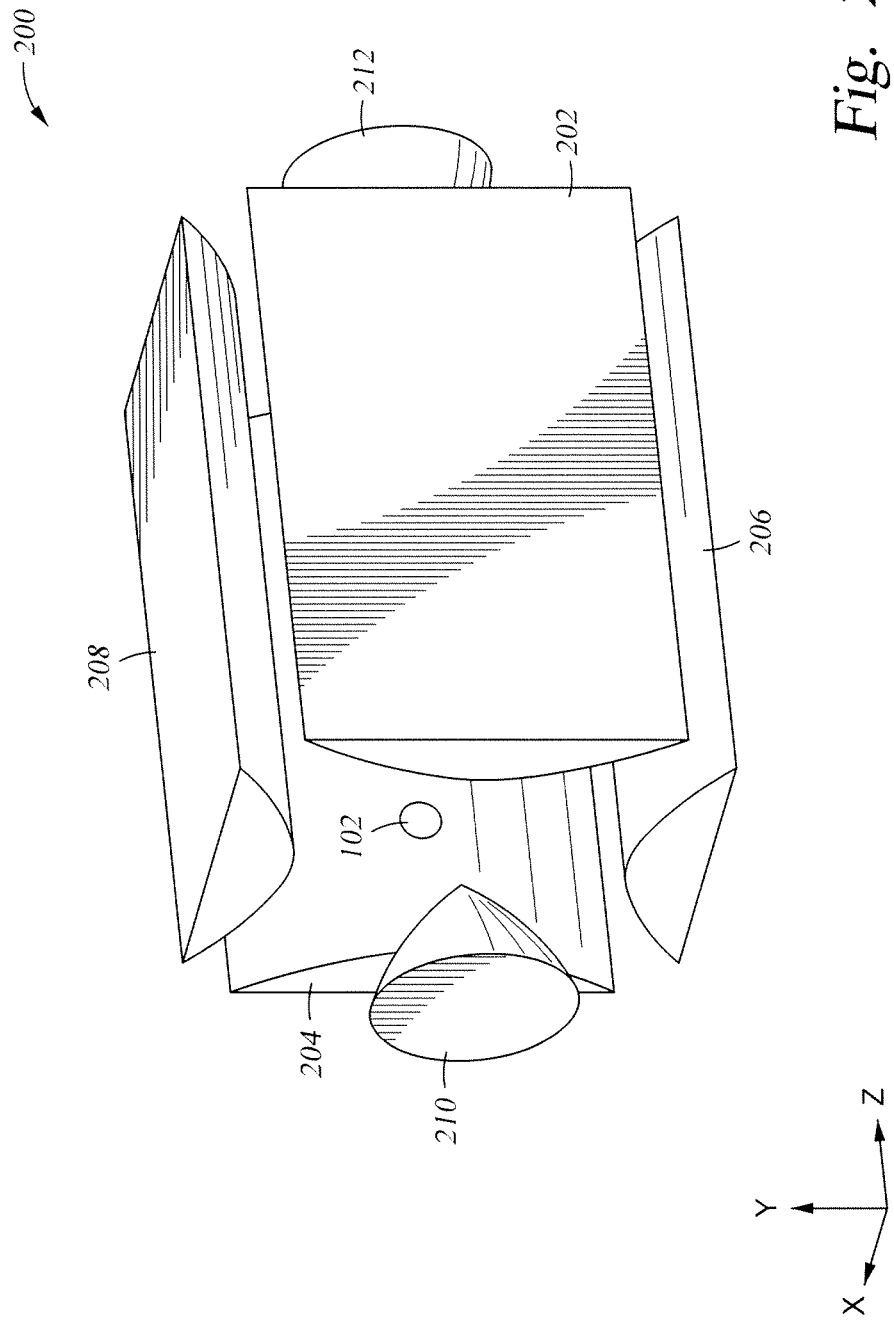
FIG. 2 depicts a schematic view of an ion trap for confining ions in a group according to one embodiment.

FIG. 2 depicts a schematic view of an ion trap 200 (also referred to as a Paul trap) for confining ions in the group 106 according to one embodiment. The confining potential is exerted by both static (DC) voltage and radio frequency (RF) voltages. A static (DC) voltage $V_S$ is applied to end-cap electrodes 210 and 212 to confine the ions along the Z-axis (also referred to as an "axial direction" or a "longitudinal direction"). The ions in the group 106 are nearly evenly distributed in the axial direction due to the Coulomb interaction between the ions. In some embodiments, the ion trap 200 includes four hyperbolically-shaped electrodes 202, 204, 206, and 208 extending along the Z-axis.

During operation, a sinusoidal voltage $V_1$ (with an amplitude $V_{RF}/2$) is applied to an opposing pair of the electrodes 202, 204 and a sinusoidal voltage $V_2$ with a phase shift of 180° from the sinusoidal voltage $V_1$ (and the amplitude $V_{RF}/2$) is applied to the other opposing pair of the electrodes 206, 208 at a driving frequency $\omega_{RF}$, generating a quadrupole potential. In some embodiments, a sinusoidal voltage is only applied to one opposing pair of the electrodes 202, 204, and the other opposing pair 206, 208 is grounded. The quadrupole potential creates an effective confining force in the X-Y plane perpendicular to the Z-axis (also referred to as a "radial direction" or "transverse direction") for each of the trapped ions, which is proportional to a distance from a saddle point (i.e., a position in the axial direction (Z-direction)) at which the RF electric field vanishes. The motion in the radial direction (i.e., direction in the X-Y plane) of each ion is approximated as a harmonic oscillation (referred to as secular motion) with a restoring force towards the saddle point in the radial direction and can be modeled by spring constants $k_x$ and $k_y$, respectively, as is discussed in greater detail below. In some embodiments, the spring constants in the radial direction are modeled as equal when the quadrupole potential is symmetric in the radial direction. However, undesirably in some cases, the motion of the ions in the radial direction may be distorted due to some asymmetry in the physical trap configuration, a small DC patch potential due to inhomogeneity of a surface of the electrodes, or the like and due to these and other external sources of distortion the ions may lie off-center from the saddle points.

Although not shown, a different type of trap is a microfabricated trap chip in which a similar approach as the one described above is used to hold or confine ions or atoms in place above a surface of the micro-fabricated trap chip. Laser beams, such as the Raman laser beams described above, can be applied to the ions or atoms as they sit just above the surface.

Figure 3:
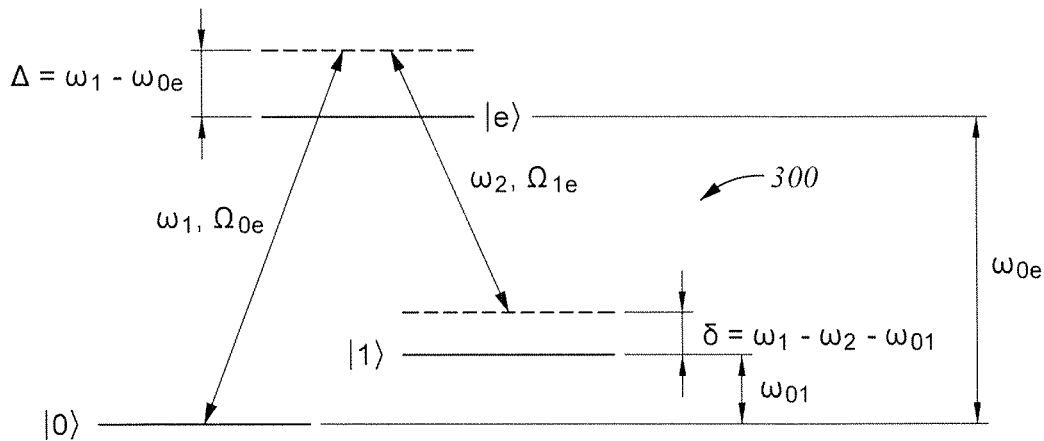
FIG. 3 depicts a schematic energy diagram of each ion in a group of trapped ions according to one embodiment.

FIG. 3 depicts a schematic energy diagram 300 of each ion in the group 106 of trapped ions according to one embodiment. Each ion in the group 106 of trapped ions is an ion having a nuclear spin I and an electron spin S such that a difference between the nuclear spin I and the electron spin S is zero. In one example, each ion may be a positive Ytterbium ion, $^{171}Yb^+$, which has a nuclear spin $$I = \frac{1}{2}$$

and the $^2S_{1/2}$ hyperfine states (i.e., two electronic states) with an energy split corresponding to a frequency difference (referred to as a "carrier frequency") of $\omega_{01}/2\pi=12.642821$ GHZ. In other examples, each ion may be a positive barium ion $^{133}Ba^+$, a positive cadmium ion $^{111}Cd^+$ or $^{113}Cd^+$, which all have a nuclear spin $$I = \frac{1}{2}$$

and the $^2S_{1/2}$ hyperfine states. A qubit is formed with the two hyperfine states, denoted as |0⟩ and |1⟩, where the hyperfine ground state (i.e., the lower energy state of the $^2S_{1/2}$ hyperfine states) is chosen to represent |0⟩. Hereinafter, the terms "hyperfine states," "internal hyperfine states," and "qubits" may be interchangeably used to represent |0⟩ and |1⟩. Each ion may be cooled (i.e., kinetic energy of the ion may be reduced) to near the motional ground state |0⟩$_m$ for any motional mode m with no phonon excitation (i.e., $n_{ph}$=0) by known laser cooling methods, such as Doppler cooling or resolved sideband cooling, and then the qubit state prepared in the hyperfine ground state |0⟩ by optical pumping. Here, |0⟩ represents the individual qubit state of a trapped ion whereas |0⟩$m$ with the subscript m denotes the motional ground state for a motional mode m of a group 106 of trapped ions.

An individual qubit state of each trapped ion may be manipulated by, for example, a mode-locked laser at 355 nanometers (nm) via the excited $^2P_{1/2}$ level (denoted as |e⟩). As shown in FIG. 3, a laser beam from the laser may be split into a pair of non-copropagating laser beams (a first laser beam with frequency $\omega_1$ and a second laser beam with frequency $\omega_2$) in the Raman configuration, and detuned by a one-photon transition detuning frequency $\Delta=\omega_1-\omega_{0e}$ with respect to the transition frequency $\omega_{0e}$ between |0⟩ and |e⟩, as illustrated in FIG. 3. A two-photon transition detuning frequency $\delta$ includes adjusting the amount of energy that is provided to the trapped ion by the first and second laser beams, which when combined is used to cause the trapped ion to transfer between the hyperfine states |0⟩ and |1⟩. When the one-photon transition detuning frequency $\Delta$ is much larger than a two-photon transition detuning frequency (also referred to simply as "detuning frequency") $\delta=\omega_1-\omega_2-\omega_{01}$ (hereinafter denoted as $\cdot \mu$, $\mu$ being a positive value), single-photon Rabi frequencies $\Omega_{0e}(t)$ and $\Omega_{1e}(t)$ (which are time-dependent, and are determined by amplitudes and phases of the first and second laser beams), at which Rabi flopping between states |0⟩ and |e⟩ and between states |1⟩ and |e⟩ respectively occur, and a spontaneous emission rate from the excited state |e⟩, Rabi flopping between the two hyperfine states |0⟩ and |1⟩ (referred to as a "carrier transition") is induced at the two-photon Rabi frequency $\Omega(t)$. The two-photon Rabi frequency $\Omega(t)$ has an intensity (i.e., absolute value of amplitude) that is proportional to hoe $\Omega_{0e}\Omega_{1e}/2\Delta$, where $\Omega_{0e}$ and $\Omega_{1e}$ are the single-photon Rabi frequencies due to the first and second laser beams, respectively. Hereinafter, this set of non-copropagating laser beams in the Raman configuration to manipulate internal hyperfine states of qubits (qubit states) may be referred to as a "composite pulse" or simply as a "pulse," and the resulting time-dependent pattern of the two-photon Rabi frequency $\Omega(t)$ may be referred to as an "amplitude" of a pulse or simply as a "pulse," which are illustrated and further described below. The detuning frequency $\delta=\omega_1-\omega_2-\omega_{01}$ may be referred to as detuning frequency of the composite pulse or detuning frequency of the pulse. The amplitude of the two-photon Rabi frequency $\Omega(t)$, which is determined by amplitudes of the first and second laser beams, may be referred to as an "amplitude" of the composite pulse.

It should be noted that the particular atomic species used in the discussion provided herein is just one example of atomic species which have stable and well-defined two-level energy structures when ionized and an excited state that is optically accessible, and thus is not intended to limit the possible configurations, specifications, or the like of an ion trap quantum computer according to the present disclosure. For example, other ion species include alkaline earth metal ions ($Be^+$, $Ca^+$, $Sr^+$, $Mg^+$, and $Ba^+$) or transition metal ions ($Zn^+$, $Hg^+$, $Cd^+$).

Figure 4:
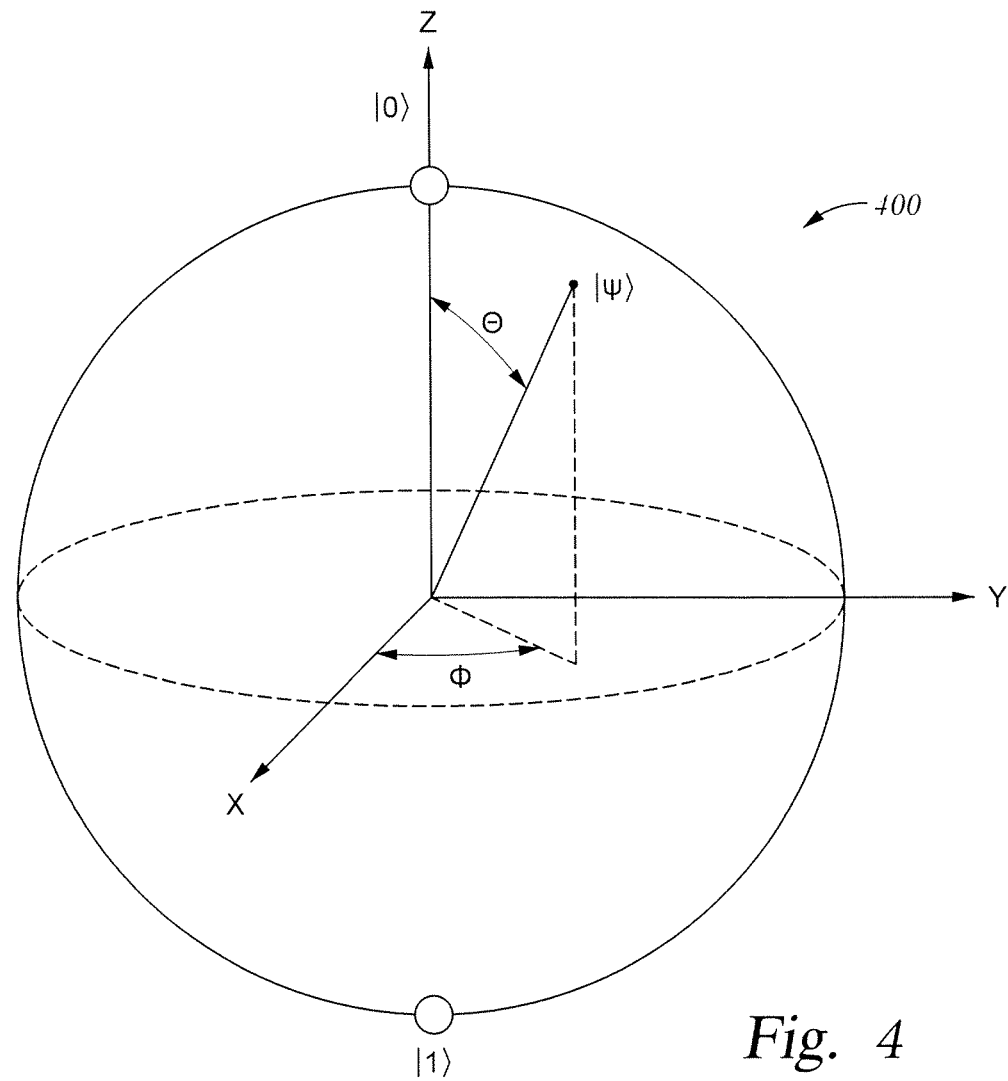
FIG. 4 depicts a qubit state of an ion represented as a point on a surface of the Bloch sphere.

FIG. 4 is provided to help visualize a qubit state of an ion is represented as a point on a surface of the Bloch sphere 400 with an azimuthal angle $\phi$ and a polar angle $\theta$. Application of the composite pulse as described above, causes Rabi flopping between the qubit state $|0\rangle$ (represented as the north pole of the Bloch sphere) and $|1\rangle$ (the south pole of the Bloch sphere) to occur. Adjusting time duration and amplitudes of the composite pulse flips the qubit state from $|0\rangle$ to $|1\rangle$ (i.e., from the north pole to the south pole of the Bloch sphere), or the qubit state from $|1\rangle$ to $|0\rangle$ (i.e., from the south pole to the north pole of the Bloch sphere). This application of the composite pulse is referred to as a "Itpulse". Further, by adjusting time duration and amplitudes of the composite pulse, the qubit state $|0\rangle$ may be transformed to a superposition state $|0\rangle+|1\rangle$, where the two qubit states $|0\rangle$ and $|1\rangle$ are added and equally-weighted in-phase (a normalization factor of the superposition state is omitted hereinafter for convenience) and the qubit state $|1\rangle$ to a superposition state $|0\rangle-|1\rangle$, where the two qubit states $|0\rangle$ and $|1\rangle$ are added equally-weighted but out of phase. This application of the composite pulse is referred to as a "$\pi/2$-pulse". More generally, a superposition of the two qubits states $|0\rangle$ and $|1\rangle$ that are added and equally-weighted is represented by a point that lies on the equator of the Bloch sphere. For example, the superposition states $|0\rangle+|1\rangle$ correspond to points on the equator with the azimuthal angle $\phi$ being zero and $\pi$, respectively. The superposition states that correspond to points on the equator with the azimuthal angle $\phi$ are denoted as $|0\rangle \pm e^{i\phi}|1\rangle$ (e.g., $|0\rangle+i|1\rangle$ for $\phi=\pm\pi/2$). Transformation between two points on the equator (i.e., a rotation about the Z-axis on the Bloch sphere) can be implemented by shifting phases of the composite pulse.

Entanglement Formation

Figure 5A:
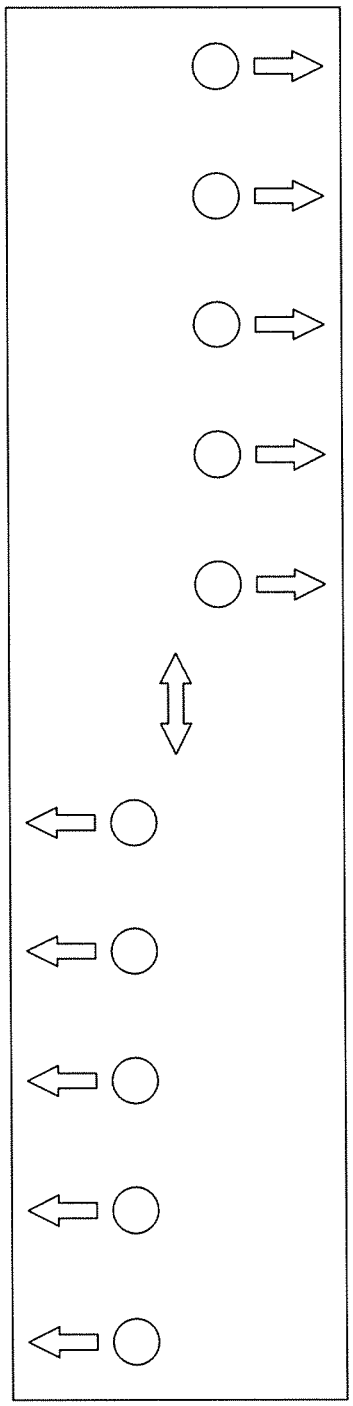
FIGS. 5A, 5B, and 5C depict a few schematic collective transverse motional mode structures of a group of five trapped ions.
Figure 5B:
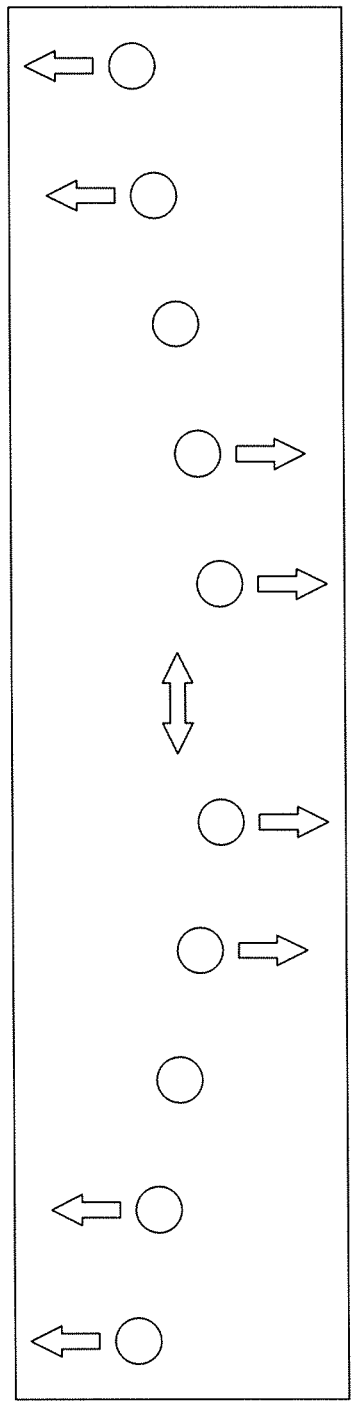
Figure 5C:
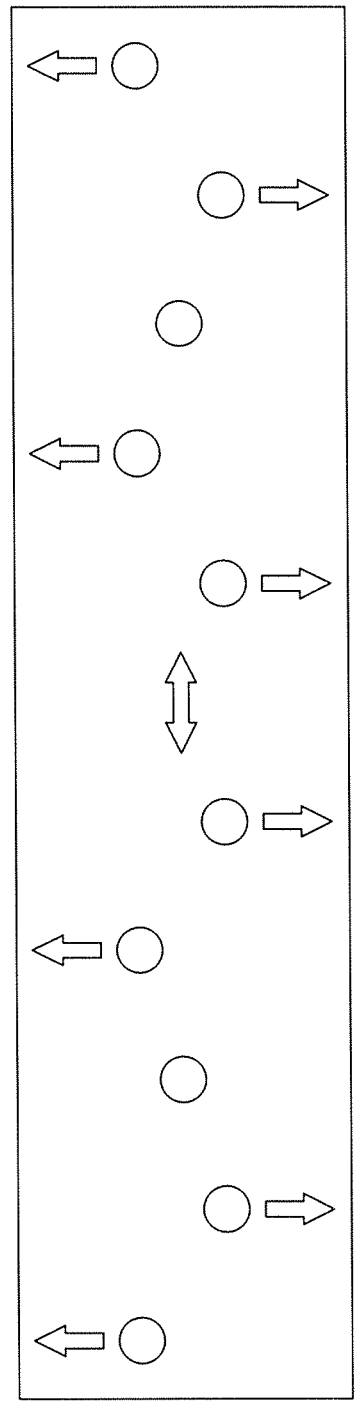

FIGS. 5A, 5B, and 5C depict a few schematic structures of collective transverse motional modes (also referred to simply as "motional mode structures") of a group 106 of five trapped ions, for example. Here, the confining potential due to a static voltage $V_S$ applied to the end-cap electrodes 210 and 212 is weaker compared to the confining potential in the radial direction. The collective motional modes of the group 106 of trapped ions in the transverse direction are determined by the Coulomb interaction between the trapped ions combined with the confining potentials generated by the ion trap 200. The trapped ions undergo collective transversal motions (referred to as "collective transverse motional modes," "collective motional modes," or simply "motional modes"), where each mode has a distinct energy (or equivalently, a frequency) associated with it. A motional mode having the moth lowest energy is hereinafter referred to as $|n_{ph}\rangle$, where $n_{ph}$ denotes the number of motional quanta (in units of energy excitation, referred to as phonons) in the motional mode, and the number of motional modes M in a given transverse direction is equal to the number of trapped ions in the group 106. FIGS. 5A-5C schematically illustrates examples of different types of collective transverse motional modes that may be experienced by five trapped ions that are positioned in a group 106. FIG. 5A is a schematic view of a common motional mode $|n_{ph}\rangle_M$ having the highest energy, where M is the number of motional modes. In the common motional mode $|n\rangle_M$, all ions oscillate in phase in the transverse direction. FIG. 5B is a schematic view of a tilt motional mode $|n_{ph}\rangle_{M-1}$ which has the second highest energy. In the tilt motional mode, ions on opposite ends move out of phase in the transverse direction (i.e., in opposite directions). FIG. 5C is a schematic view of a higher-order motional mode $|n_{ph}\rangle_{M-3}$ which has a lower energy than that of the tilt motional mode $|n_{ph}\rangle_{M-1}$, and in which the ions move in a more complicated mode pattern.

It should be noted that the particular configuration described above is just one among several possible examples of a trap for confining ions according to the present disclosure and does not limit the possible configurations, specifications, or the like of traps according to the present disclosure. For example, the geometry of the electrodes is not limited to the hyperbolic electrodes described above. In other examples, a trap that generates an effective electric field causing the motion of the ions in the radial direction as harmonic oscillations may be a multi-layer trap in which several electrode layers are stacked and an RF voltage is applied to two diagonally opposite electrodes, or a surface trap in which all electrodes are located in a single plane on a chip. Furthermore, a trap may be divided into multiple segments, adjacent pairs of which may be linked by shuttling one or more ions, or coupled by photon interconnects. A trap may also be an array of individual trapping regions arranged closely to each other on a micro-fabricated ion trap chip, such as the one described above. In some embodiments, the quadrupole potential has a spatially varying DC component in addition to the RF component described above.

Figure 6A:
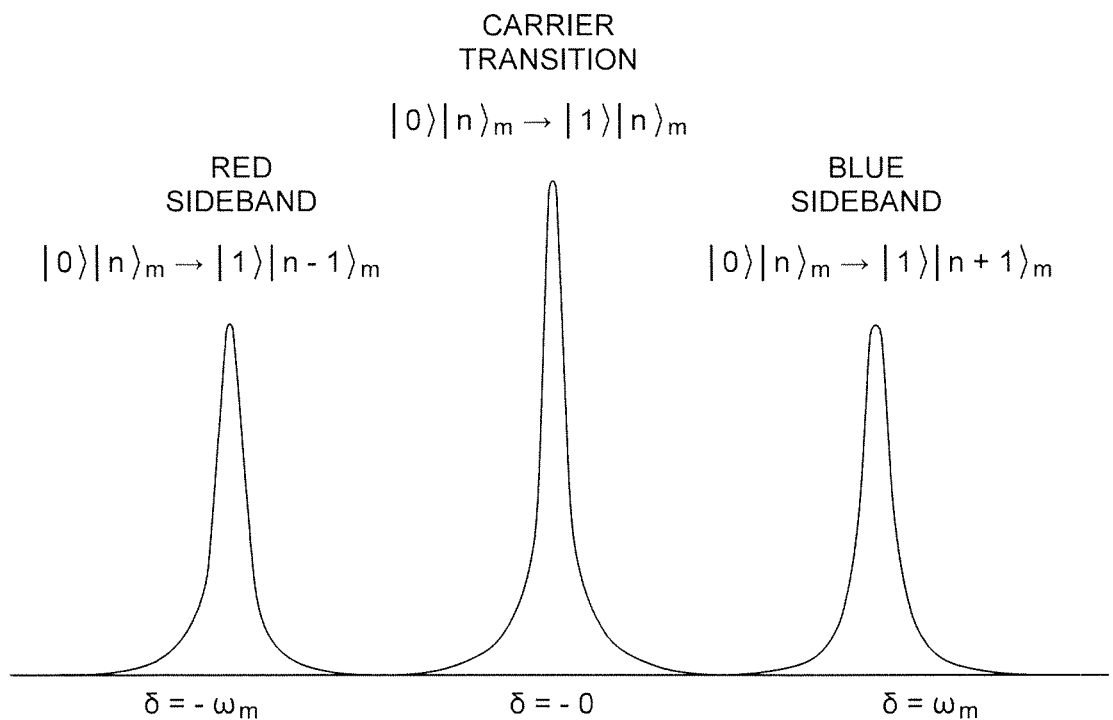
FIGS. 6A and 6B depict schematic views of motional sideband spectrum of each ion and a motional mode according to one embodiment.
Figure 6B:
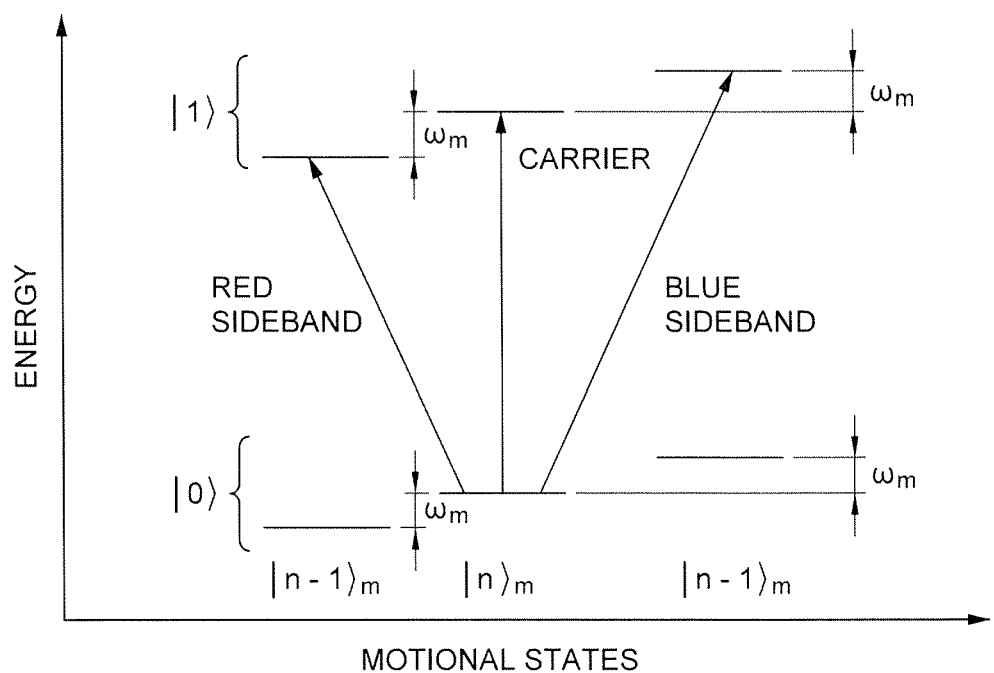

In an ion trap quantum computer, the motional modes may act as a data bus to mediate entanglement between two qubits and this entanglement is used to perform an XX gate operation. That is, each of the two qubits is entangled with the motional modes, and then the entanglement is transferred to an entanglement between the two qubits by using motional sideband excitations, as described below. FIGS. 6A and 6B schematically depict views of a motional sideband spectrum for an ion in the group 106 in a motional mode $|n_{ph}\rangle_M$ having frequency $\omega_m$ according to one embodiment. As illustrated in FIG. 6B, when the detuning frequency of the composite pulse is zero (i.e., a frequency difference between the first and second laser beams is tuned to the carrier frequency, $\delta=\omega_1-\omega_2-\omega_{01}=0$), simple Rabi flopping between the qubit states $|0\rangle$ and $|1\rangle$ (carrier transition) occurs. When the detuning frequency of the composite pulse is positive (i.e., the frequency difference between the first and second laser beams is tuned higher than the carrier frequency, $\delta=\omega_1-\omega_2-\omega_{01}=\mu>0$, referred to as a blue sideband), Rabi flopping between combined qubit-motional states $|0\rangle|n_{ph}\rangle_m$ and $|1\rangle|n_{ph}+1\rangle_m$ occurs (i.e., a transition from the m-th motional mode with n-phonon excitations denoted by $|n_{ph}\rangle_m$ to the m-th motional mode with ($n_{ph}$+1)-phonon excitations denoted by $|n_{ph}+1\rangle_m$ occurs when the qubit state $|0\rangle$ flips to $|1\rangle$). When the detuning frequency of the composite pulse is negative (i.e., the frequency difference between the first and second laser beams is tuned lower than the carrier frequency by the frequency $\omega_m$ of the motional mode $|n_{ph}\rangle_m$, $\delta=\omega_1-\omega_2-\omega_{01}=-\mu<0$, referred to as a red sideband), Rabi flopping between combined qubit-motional states $|0\rangle|n_{ph}\rangle_m$ and $|1\rangle|n_{ph}-1\rangle_m$ occurs (i.e., a transition from the motional mode $|n_{ph}\rangle_m$ to the motional mode $|n_{ph}-1\rangle_m$ with one less phonon excitations occurs when the qubit state $|0\rangle$ flips to $|1\rangle$). A $\pi/2$-pulse on the blue sideband applied to a qubit transforms the combined qubit-motional state $|0\rangle|n_{ph}\rangle_m$ into a superposition of $|0\rangle|n_{ph}\rangle_m$ and $|1\rangle|n_{ph}+1\rangle_m$. A $\pi/2$-pulse on the red sideband applied to a qubit transforms the combined qubit-motional $|0\rangle|n_{ph}\rangle_m$ into a superposition of $|0\rangle|n_{ph}\rangle$, and $|1\rangle|n_{ph}-1\rangle$. When the two-photon Rabi frequency $\Omega(t)$ is smaller as compared to the detuning frequency $\delta=\omega_1-\omega_2-\omega_{01}=\pm\mu$, the blue sideband transition or the red sideband transition may be selectively driven. Thus, a qubit can be entangled with a desired motional mode by applying the right type of pulse, such as a $\pi/2$-pulse, which can be subsequently entangled with another qubit, leading to an entanglement between the two qubits that is needed to perform an XX-gate operation in an ion trap quantum computer.

By controlling and/or directing transformations of the combined qubit-motional states as described above, an XX-gate operation may be performed on two qubits (i-th and j-th qubits). In general, the XX-gate operation (with maximal entanglement) respectively transforms two-qubit states $|0\rangle_i|0\rangle_j$, $|0\rangle_i|1\rangle_j$, $|1\rangle_i|0\rangle_j$, and $|1\rangle_i|1\rangle_j$ as follows:

$|0\rangle_i|0\rangle_j \rightarrow |0\rangle_i|0\rangle_j - i|1\rangle_i|1\rangle_j$ $|0\rangle_i|1\rangle_j \rightarrow |0\rangle_i|1\rangle_j - i|1\rangle_i|0\rangle_j$ $|1\rangle_i|0\rangle_j \rightarrow -i|0\rangle_i|1\rangle_j + |1\rangle_i|0\rangle_j$ $|1\rangle_i|1\rangle_j \rightarrow -i|0\rangle_i|0\rangle_j + |1\rangle_i|1\rangle_j$ For example, when the two qubits (i-th and j-th qubits) are both initially in the hyperfine ground state $|0\rangle$ (denoted as $|0\rangle_i|0\rangle_j$) and subsequently a $\pi/2$-pulse on the blue sideband is applied to the i-th qubit, the combined state of the i-th qubit and the motional mode $|0\rangle_i|n_{ph}\rangle_m$ is transformed into a superposition of $|0\rangle_i|n_{ph}\rangle_m$ and $|1\rangle_i|n_{ph}+1\rangle_m$, and thus the combined state of the two qubits and the motional mode is transformed into a superposition of $|0\rangle_i|0\rangle_j|n_{ph}\rangle_m$ and $|1\rangle_i|0\rangle_j|n_{ph}+1\rangle_m$. When a $\pi/2$-pulse on the red sideband is applied to the j-th qubit, the combined state of the j-th qubit and the motional mode $|0\rangle_j|n_{ph}\rangle_m$ is transformed to a superposition of $|0\rangle_j|n_{ph}\rangle_m$ and $|1\rangle_j|n_{ph}-1\rangle_m$ and the combined state $|0\rangle_j|n_{ph}+1\rangle_m$ is transformed into a superposition of $|0\rangle_j|n_{ph}+1\rangle_m$ and $|1\rangle_j|n_{ph}\rangle_m$.

Thus, applications of a $\pi/2$-pulse on the blue sideband on the i-th qubit and a $\pi/2$-pulse on the red sideband on the j-th qubit may transform the combined state of the two qubits and the motional mode $|0\rangle_i|0\rangle_j|n_{ph}\rangle_m$ into a superposition of $|0\rangle_i|0\rangle_j|n_{ph}\rangle_m$ and $|1\rangle_i|1\rangle_j|n_{ph}\rangle_m$, the two qubits now being in an entangled state. For those of ordinary skill in the art, it should be clear that two-qubit states that are entangled with motional mode having a different number of phonon excitations from the initial number of phonon excitations $n_{ph}$ (i.e., $|1\rangle_i|0\rangle_j|n_{ph}+1\rangle_m$ and $|0\rangle_i|1\rangle_j|n_{ph}-1\rangle_m$) can be removed by a sufficiently complex pulse sequence, and thus the combined state of the two qubits and the motional mode after the XX-gate operation may be considered disentangled as the initial number of phonon excitations $n_{ph}$ in the m-th motional mode stays unchanged at the end of the XX-gate operation. Thus, qubit states before and after the XX-gate operation will be described below generally without including the motional modes.

More generally, the combined state of i-th and j-th qubits transformed by the application of pulses on the sidebands for duration $\tau$ (referred to as a "gate duration"), having amplitudes $\Omega^{(i)}$ and $\Omega^{(j)}$ and detuning frequency $\mu$, can be described in terms of an entangling interaction $\chi^{(i,j)}(\tau)$ as follows:

$|0\rangle_i|0\rangle_j \rightarrow \cos(2\chi^{(i,j)}(\tau))|0\rangle_i|0\rangle_j - i\sin(2\chi^{(i,j)}(\tau))|1\rangle_i|1\rangle_j$ $|0\rangle_i|1\rangle_j \rightarrow \cos(2\chi^{(i,j)}(\tau))|0\rangle_i|1\rangle_j - i\sin(2\chi^{(i,j)}(\tau))|1\rangle_i|0\rangle_j$ $|1\rangle_i|0\rangle_j \rightarrow -i\sin(2\chi^{(i,j)}(\tau))|0\rangle_i|1\rangle_j + \cos(2\chi^{(i,j)}(\tau))|1\rangle_i|0\rangle_j$ $|1\rangle_i|1\rangle_j \rightarrow -i\sin(2\chi^{(i,j)}(\tau))|0\rangle_i|0\rangle_j + \cos(2\chi^{(i,j)}(\tau))|1\rangle_i|1\rangle_j$ where, $$\chi^{(i,j)}(\tau) = -4\sum_{m=1}^{M}\eta_m^{(i)}\eta_m^{(j)}\int_0^\tau dt_2 \int_0^{t_2} dt_1 \Omega^{(i)}(t_2)\Omega^{(j)}(t_1)\cos(\mu t_2)\cos(\mu t_1)\sin[\omega_m(t_2-t_1)]$$

and $n_m^{(i)}$ is the Lamb-Dicke parameter that quantifies the coupling strength between the i-th ion and the m-th motional mode having the frequency $\omega_m$, and M is the number of the motional modes (equal to the number N of ions in the group 106).

The entanglement interaction between two qubits described above can be used to perform an XX-gate operation. The XX-gate operation (XX gate) along with single-qubit operations (R gates) forms a set of gates {R, XX} that can be used to build a quantum computer that is configured to perform desired computational processes. Among several known sets of logic gates by which any quantum algorithm can be decomposed, a set of logic gates, commonly denoted as {R, XX}, is native to a quantum computing system of trapped ions described herein. Here, the R gate corresponds to manipulation of individual qubit states of trapped ions, and the XX gate (also referred to as an "entangling gate") corresponds to manipulation of the entanglement of two trapped ions.

To perform an XX-gate operation between i-th and j-th qubits, pulses that satisfy the condition $\chi^{(i,j)}(\tau)=\theta^{(i,j)}$ ($0<\theta^{(i,}$ j)≤π/8) (i.e., the entangling interaction $\chi^{(i,j)}(\tau)$ has a desired value $\theta^{(i,j)}$, referred to as condition for a non-zero entanglement interaction) are constructed and applied to the i-th and the j-th qubits. The transformations of the combined state of the i-th and the j-th qubits described above corresponds to the XX-gate operation with maximal entanglement when $\theta^{(i,j)}=\pi/8$. Amplitudes $\Omega^{(i)}(t)$ and $\Omega^{(j)}(\tau)$ of the pulses to be applied to the i-th and the j-th qubits are control parameters that can be adjusted to ensure a non-zero tunable entanglement of the i-th and the j-th qubits to perform a desired XX gate operation on i-th and j-th qubits.

Hybrid Quantum-Classical Computing System

In a hybrid quantum-classical computing system, a quantum computer can generally be used as a domain-specific accelerator that may be able to accelerate certain computational tasks beyond the reach of what classical computers can do. As mentioned above, the terms "quantum computer" and "quantum processor" can be used interchangeably. Examples of such computational tasks include Fourier transformation(s) that represents a time dependent function in a frequency domain, or a spatial function in a reciprocal space (also referred to as "k-space"). Fourier transformation is used in a wide range of applications, such as computer simulations of atoms and molecules (i.e., physical systems), and varieties of image and signal processing applications. However, complexity of Fourier transformation increases drastically as a problem size (e.g., the number of atoms/molecules) increases and may be unsolvable or be too complex to complete in a reasonable amount of time by a classical computer alone.

In one example, a hybrid quantum-classical computing system can be used for performing molecular dynamics (MD) simulations of a physical system having particles that exert force on each other via short-range and long-range interactions. Examples of such physical systems include ionic fluids, DNA strands, proteins, (poly) electrolyte solutions, colloids, or molecular models with partial charge. The dynamics of such a physical system is dictated by the energetics of the system and the primary contribution to the energies of the system comes from the Coulomb interaction among particles. Thus, methods for computing inter-particle interaction energies due to the Coulomb interaction among particles are described herein.

It should be noted that the example embodiments described herein are just some possible examples of a hybrid quantum-classical computing system according to the present disclosure and do not limit the possible configurations, specifications, or the like of hybrid quantum-classical computer systems according to the present disclosure. For example, a hybrid quantum-classical computing system according to the present disclosure can be applied to other types of computer simulations or image/signal processing in which Fourier transformation contributes to the computational complexity and can be accelerated by use of a quantum processor.

Figure 7:
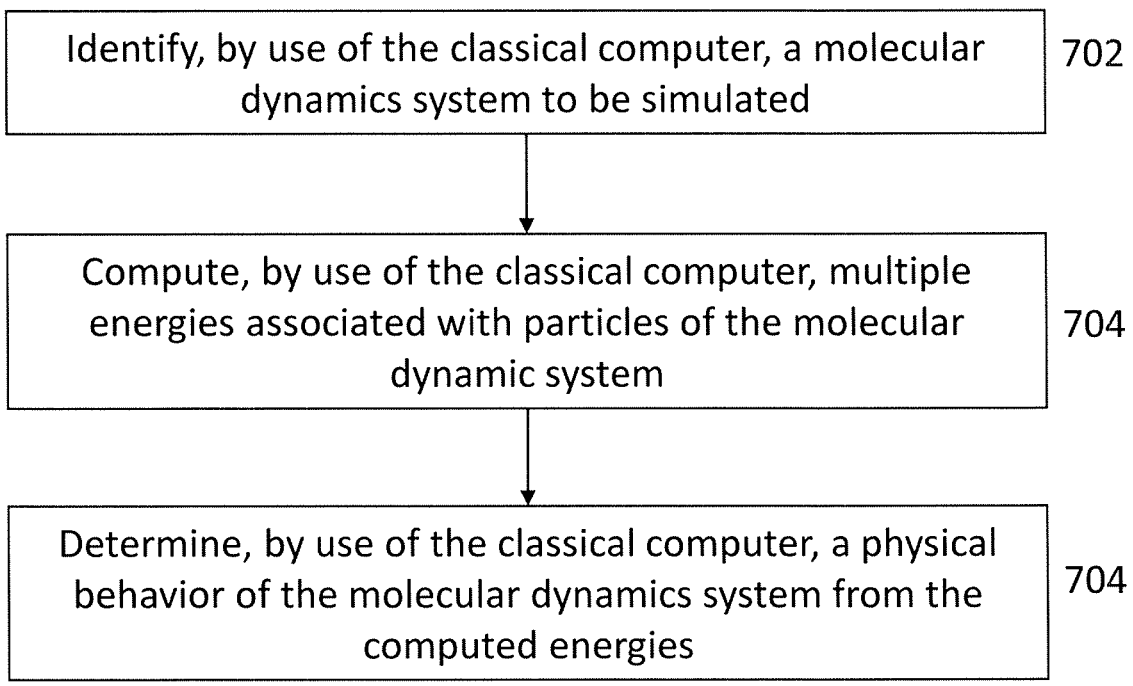
FIG. 7 depicts a flowchart illustrating a method 700 of performing computation using a hybrid quantum-classical computing system comprising a classical computer and a quantum processor.

FIG. 7 depicts a flowchart illustrating a method 700 of performing one or more computations using a hybrid quantum-classical computing system comprising a classical computer and a quantum processor.

In block 702, by the classical computer 102, a molecular dynamics system to be simulated is identified, for example, by use of user input applied using a user interface, such as graphics processing unit (GPU), of the classical computer 102, and/or by retrieving information from the memory of the classical computer 102.

In block 704, by the classical computer 102, multiple energies associated with particles of the molecular dynamics system are computed as part of the simulation. The computing of the multiple energies are based on an Ewald summation method. The computing of the multiple energies include partially offloading the computing of the multiple energies that are based on Fourier transformations to the quantum processor. The processes performed in block 704 are further described below.

In block 706, by use of the classical computer 102, a physical behavior of the molecular dynamics system is generated from the computed energies. The results of block 706 can then be provided to a user as discussed further below.

Figure 8:
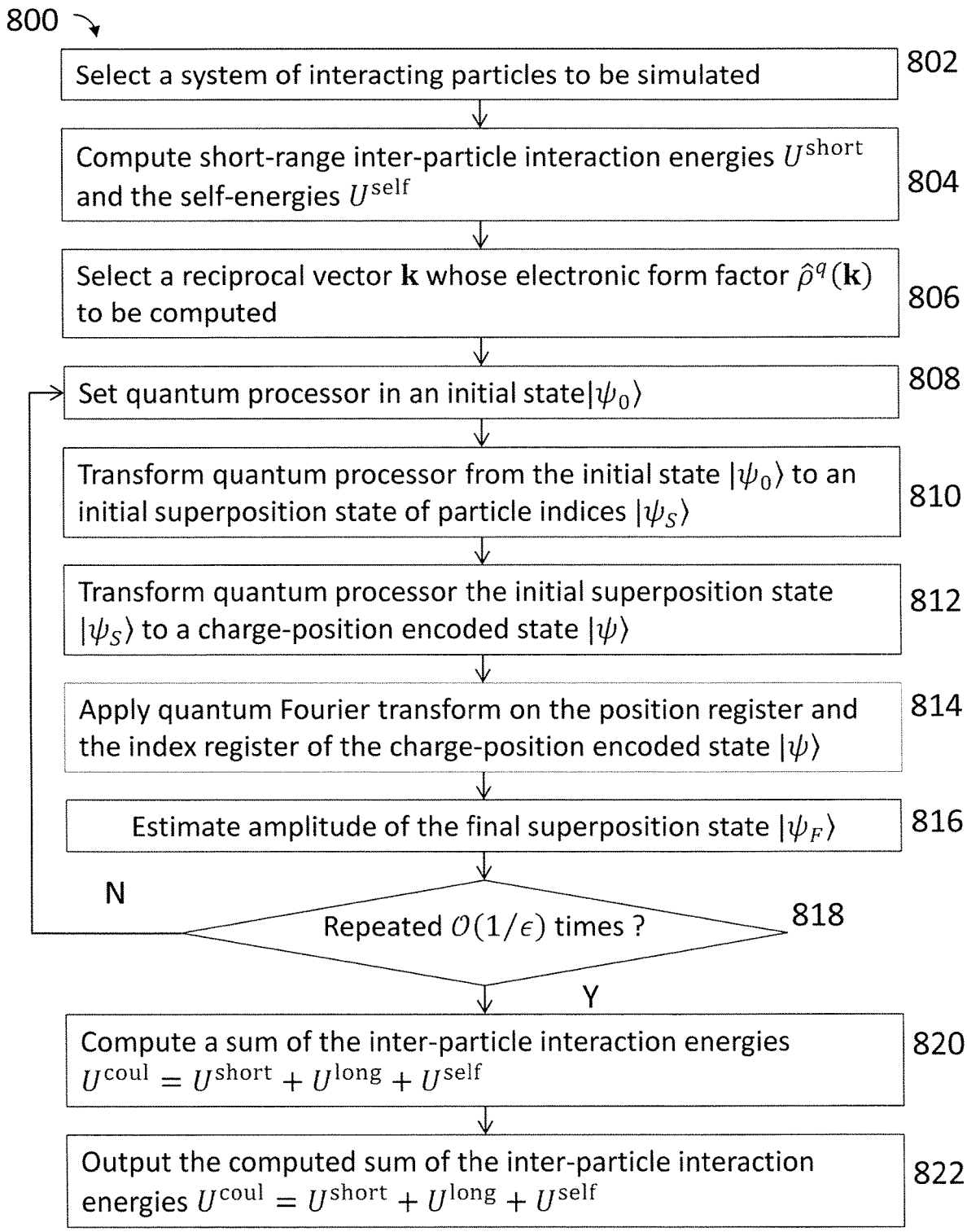
FIG. 8 depicts a flowchart illustrating a method of obtaining energies of a system having interacting particles by molecular dynamics (MD) simulations according to one embodiment.

FIG. 8 depicts a flowchart illustrating a method 800 of computing multiple energies associated with particles of the molecular dynamics system as part of the molecular dynamics (MD) simulations as shown in block 704 above. In this example, the quantum processor is based on the group 106 of trapped ions, in which the two hyperfine states of each of the trapped ions form a qubit. Thus, the trapped ions form the qubits that provide the computing core of the quantum processor or quantum computer.

In the molecular dynamics (MD) simulations, a bulk material that is to be analyzed based on simulations is typically modeled as an infinite system in which a finite system (referred to as a "primitive cell") of N interacting particles is duplicated with periodic boundary conditions imposed. The N interacting particles may have long-range interaction (e.g., Coulomb interaction) with one another. It is widely accepted that truncating the long-range interactions introduces unphysical artifacts in calculating inter-particle interaction energies. Thus, calculation of the inter-particle interaction energies would require summation of the long-range interactions of all pairs among N interacting particles, leading to an increase in the computational complexity as $\mathcal{O}(N^2)$ if the long-range interactions are directly summed. The Ewald summation method allows efficient calculation of inter-particle interaction energies due to the long-range interactions with an increase in the computational complexity as $\mathcal{O}(N^{3/2})$ and has become a standard method to efficiently simulate a group of particles having long-range interaction.

It is considered herein N interacting, classical particles, evolving according to the laws of classical physics. Each particle has a well-defined position and momentum at any time during the simulation.

A sum of the inter-particle interaction energies $U^{coul}$ due to pairwise interactions, e.g., Coulomb interaction, is given by $$U^{coul} = \frac{1}{2}\sum_{t \in \mathbb{Z}^3}\sum_{i,j=0}^{N-1}\left|\frac{q_i q_j}{r_i - r_j + tL}\right|$$

where i and j denote the particle indices (i=0, 1, 2, ..., N−1, j=0, 1, 2, ..., N−1) in a primitive cell of a cubic shape with an edge length of L, $r_i=(r_x^{(i)}, r_y^{(i)}, r_z^{(i)})$ and $r_j=(r_x^{(j)}, r_y^{(j)}, r_z^{(j)})$ denote the positions of the respective particles i and j, $q_i$ and $q_j$ denote the charges of the respective particles i and j, and $t=(t_x, t_y, t_z)$ denote a vector of integer indices for each duplicated primitive cell.

In the Ewald summation method, a charge distribution $\rho(r)$ at a position r in the primitive cell, for example, a sum of N point charges (each of which is described by a Dirac delta function $\delta(r-r_i)$), $$\rho(r) = \sum_{i=0}^{N-1} q_i \delta(r - r_i),$$

is replaced by a sum of a screened charge distribution $\rho^S(r)$ (i.e., each point charge is smeared) and a cancelling charge distribution $\rho^L(r)$ to compensate for the screened charge distribution $\rho^S(r)$, given by $$\rho(r) = \rho^S(r) + \rho^L(r),$$

where $$\rho^S(r) = \sum_{i=0}^{N-1} q_i (\delta(r - r_i) - W_\alpha(r - r_i)),$$

with a screening function $W_\alpha(r-r_i)$. The screening function $W_\alpha(r-r_i)$ may be, for example, a Gaussian screen function, $$W_\alpha(r - r_i) = \left(\frac{\alpha}{\sqrt{\pi}}\right)^3 \exp(-\alpha^2 |r - r_i|^2),$$

where the parameter $\alpha > 0$ defines a width of the screening. The screened charge distribution $\rho^S(r)$ screens the interaction between point charges that are separated more than the parameter $\alpha$ (that is, the inter-particle interaction due to the screened charge distribution $\rho^S(r)$ is short-range) and subsequently leads to a rapid convergence in calculating inter-particle interaction energies due to the screened charge distribution $\rho^S(r)$. To compensate a difference between the contribution to the inter-particle interaction energies due to the screened charge distribution $\rho^S(r)$ and that of the (original) charge distribution $\rho(r)$, the cancelling charge distribution $\rho^L(r)$ having the same charge sign as the point charge, $$\rho^L(r) = \sum_{i=0}^{N-1} q_i W_\alpha(r - r_i),$$

is added. The inter-particle interaction due to the cancelling charge distribution $\rho^L(r)$ is long range, and the contribution to the inter-particle interaction energies due to the cancelling charge distribution $\rho^L(r)$ is typically calculated in the reciprocal space.

Thus, the inter-particle interaction energies $U^{coul}$ is a sum of short-range inter-particle interaction energies $U^{short}$ due to the screened charge distribution $\rho^S(r)$, $$U^{short} = \frac{1}{2} \sum_{t \in \mathbb{Z}^3} \sum_{i,j=0}^{N-1} \left|\frac{q_i q_j}{r_i - r_j + tL}\right| \mathrm{erfc}(\alpha |r_i - r_j + tL|^2),$$

long-range inter-particle interaction energies $U^{long}$, $$U^{long} = \frac{2\pi}{L^3} \sum_{k=0}^{K} \frac{1}{k^2} \exp\left(-\frac{k^2}{4\alpha^2}\right) |\hat{\rho}^q(k)|^2,$$

and self-energies $U^{self}$, $$U^{self} = \frac{\alpha}{\pi^{1/2}} \sum_{i=0}^{N-1} q_i^2.$$

In the long-range interaction energies $U^{long}$, the Fourier transform of the charge density, $$\hat{\rho}^q(k) = \sum_{j=0}^{N-1} q_j e^{ik \cdot r_j},$$

is the electric form factor well known in the art and also referred to as "structure factor S(k)" in the context of crystallography. The reciprocal vectors k is defined as $k=(k_x, k_y, k_z)=(2\pi n_x/L, 2\pi n_y/L, 2\pi n_z/L)$, where $n_x$, $n_y$, and $n_z$ are integers, and K is the maximal k. The maximal k to be considered, i.e., K, is typically chosen to ensure the simulation is accurate to within the desired upper-bound error $\delta$.

It is known in the state of the art the calculation of $U^{coul} \sim U^{short} + U^{long} + U^{self}$ is required for the MD simulation of classical particles in the method 700 described hereinafter, conventionally performed on classical computing systems. Some aspects of the calculation are computationally expensive on classical computers.

The calculation of the electric form factor $\hat{\rho}^q(k)$ in the long-range interaction energies $U^{long}$ involves Fourier transformation and can be accelerated by use of a quantum processor. As described herein, the methods 700 and 800 provide an improvement in computational complexity over the conventional classical MD simulation. As the number of interacting particles N in a primitive cell increases, the computational complexity by the method 800 scales as $\mathcal{O}(N^{25/17}(\log N)^2)$, while that by the conventional classical MD simulation scales as $\mathcal{O}(N^{3/2})$.

In block 802, by the classical computer 102, a group of interacting particles to be simulated is selected, for example, by use of a user interface, such as graphics processing unit (GPU), of the classical computer 102, or retrieved from the memory of the classical computer 102. Specifically, a size of the primitive cell (e.g. edge lengths $L_x$, $L_y$, and $L_z$), the number of interacting particles N in the primitive cell, positions of the N interacting particles in the primitive cell, a charge distribution p (r) at a position r in the primitive cell, a type of inter-particle interactions among the N interacting particles (e.g., Coulomb interaction), a screening function $W_\alpha(r-r_i)$, the number of qubits Γ to encode a position $r_i$ of a charge $q_i$, a desired upper-bound error & in discretizing the position $r_i$, and a desired upper-bound error & in an amplitude estimation (in block 816) to be used in the MD simulation are selected and saved in the memory of the classical computer 102.

In block 804, by the classical computer 102, the short-range inter-particle interaction energies $U^{short}$ and the self-energies $U^{self}$ are computed by conventional methods known in the art.

In block 806, by the classical computer 102, a reciprocal vector k whose electronic form factor pa (k) to be computed on the quantum processor 106 is selected.

In block 808, by the system controller 104, the quantum processor (i.e., the group of ions 106) is set in an initial state $|\psi_0\rangle = |0\rangle|0\rangle|0\rangle$. The first quantum register (referred to also as an "index register" hereinafter) is formed of log N qubits to encode particle indices j(=0, 1, 2, ..., N−1). The second quantum register (referred to also as a "position register"

hereinafter) is formed of $\mathcal{O}(\Gamma)$ qubits to encode the positions $r_j=(r_x^{(j)}, r_y^{(j)}, r_z^{(j)})$ of particles $j(=0, 1, 2, \ldots, N-1)$, by discretizing the edge lengths $L_x$, $L_y$, and $L_z$ of a primitive cell into sufficiently dense grids.

The third quantum register is formed of one qubit to encode a charge $q_j$ at a position $r_j$, in an example where the charges $q_j$ are scaled by an appropriate factor and can to take $-1$ or $+1$. In the initial state $|\psi_0\rangle$, all qubits in the first, second, and third quantum registers are prepared in state $|0\rangle$, for example, the hyperfine ground state $|0\rangle$, by optical pumping in an exemplary quantum computer with trapped ions.

In block 810, by the system controller 104, the quantum processor is transformed from the initial state $|\psi_0\rangle|0\rangle|0\rangle|0\rangle$ to an initial superposition state of particle indices $$j(=0, 1, 2, \ldots, N-1), |\psi_S\rangle = \frac{1}{\sqrt{N}}\sum_{j=0}^{N-1}|j\rangle|0\rangle|0\rangle.$$

The initial superposition state $|\psi_S\rangle$ can be set by application of a proper combination of single-qubit operations and two-qubit operations to the log N qubits of the index register in the initial state $|\psi_0\rangle=|0\rangle|0\rangle|0\rangle$.

In block 812, by the system controller 104, the quantum processor is transformed from the initial superposition state $|\psi_S\rangle$ to a charge-position encoded state $|2\rangle$. An example method for the preparation of charge-position encoded state $|\psi\rangle$ uses a Quantum Random Access Memory (QRAM) operation that includes two operations, $\mathcal{D}_r$ and $\mathcal{D}_q$, and a $\pi$-pulse around the Z-axis. A QRAM, based on the bucket-brigade, can create a superposition of quantum states of I qubits in time $\mathcal{O}(\Gamma^2)$.

First, the operations $\mathcal{D}_r$ and $\mathcal{D}_q$ are applied to the initial superposition state $|\psi_S\rangle$. The operations $\mathcal{D}_r$ and $\mathcal{D}_q$ respectively retrieve the positions $r_j=(r_x^{(j)}, r_y^{(j)}, r_z^{(j)})$ and charges $q_j$ from either the (classical) memory of the classical computer 102 or a quantum memory (formed of qubits) of the quantum processor 106 and encode the positions $r_j=(r_x^{(j)}, r_y^{(j)}, r_z^{(j)})$ in the position register and the charges $q_j$ into the third register. That is, the initial superposition state $|\psi_S\rangle$ is transformed to an intermediate superposition state $|\psi_I\rangle$ by the operations $\mathcal{D}_r$ and $\mathcal{D}_q$, $$|\psi_S\rangle \xrightarrow{\mathcal{D}_r} \frac{1}{\sqrt{N}}\sum_{j=0}^{N-1}|j\rangle|r_j\rangle|0\rangle \xrightarrow{\mathcal{D}_q} |\psi_I\rangle = \frac{1}{\sqrt{N}}\sum_{j=0}^{N-1}|j\rangle|r_j\rangle\left|\frac{1-q_j}{2}\right\rangle,$$

where a tensor product of the three sub-registers $|r_x^{(i)}\rangle \otimes |r_x^{(i)}\rangle \otimes |r_x^{(i)}\rangle$ is simply be referred to as $|r_i\rangle$.

The transformations by the operations $\mathcal{D}_r$ and $\mathcal{D}_q$ can be implemented by the application of a combination of gate operations to the quantum processor 106 by the system controller 104. In some embodiments, the combination of gate operations include single-qubit gate operations and two-qubit gate operations.

Subsequently, a $\pi$-pulse around the Z-axis (referred to as an operation Z) is applied on the third quantum register (i.e., a rotation of the third quantum register qubit about the Z-axis on the Bloch sphere), which transforms the intermediate superposition state $|\psi_I\rangle$ to a phased intermediate superposition state $|\psi_I'\rangle$, $$|\psi_I\rangle \xrightarrow{Z} |\psi_I'\rangle = \frac{1}{\sqrt{N}}\sum_{j=0}^{N-1}(-1)^{\frac{1-q_j}{2}}|j\rangle|r_j\rangle\left|\frac{1-q_j}{2}\right\rangle.$$

In the example described herein, the charges $q_j$ are either $-1$ or $+1$, and thus the phase $$(-1)^{\frac{1-q_j}{2}}$$

equals $q_j$. The operation Z can be implemented by the application of a combination of single-qubit gate operations by the system controller 104.

When the charges $q_j$ take values other than or any other either $-1$ or $+1$, a combination of suitable single-qubit gate operations is applied to the third register to bring out the charges q; from the third register to amplitudes of the third register.

Finally, an inverse QRAM operation $\mathcal{D}_q^\dagger$ is applied to the third register of the phased intermediate superposition state $|\psi_I'\rangle$, which transforms the phased intermediate superposition state $|\psi_I'\rangle$ to a charge-position encoded state $|\psi\rangle$, $$|\psi_I'\rangle \xrightarrow{\mathcal{D}_q^\dagger} |\psi\rangle = \frac{1}{\sqrt{N}}\sum_{j=0}^{N-1}q_j|j\rangle|r_j\rangle|0\rangle,$$

where the charge charges q; are encoded as amplitudes and positions $r_i=(r_x^{(i)}, r_y^{(i)}, r_z^{(i)})$ of the charges $q_i$ are mapped in the position register. The complexity of the preparation of charge-position encoded state $|\psi\rangle$ when aided by a QRAM scales as $\mathcal{O}(\Gamma^2)$, where $\Gamma$ is the number of qubits in the position register.

In block 814, by the system controller 104, quantum Fourier transform (QFT) is applied on the position register (referred to as an operation $\mathcal{F}_r$) and on the index register (referred to as an operation $\mathcal{F}_j$) of the charge-position encoded state $|\psi\rangle$ in the quantum processor 106. QFT differs from the classical Fourier transform in that QFT operates on a superposition state of multiple quantum states and produces a superposition state of different quantum states as the output. QFT works using interference, either constructively or destructively, depending on amplitudes and phases of the multiple quantum states in the superposition state. Due to this difference, QFT reduces computational complexity such as fewer number of required gate operations than the classical Fourier transform (e.g., $\mathcal{O}(n^2)$ gates for exact QFT or $\mathcal{O}(n \log(n))$ for an approximate QFT versus $\mathcal{O}(n2^n)$ gates for a classical computer, where n is the size of a register).

The operations $\mathcal{F}_r$ and $\mathcal{F}_j$ bring the charge-position encoded state $|\psi\rangle$ to a final superposition state (also referred to as a "Fourier transformed superposition state") $|\psi_F\rangle$, $$|\psi\rangle \xrightarrow{\mathcal{F}_r} \frac{1}{\sqrt{N}M^{3/2}}\sum_{k=0}^{K}\left(\sum_{j=0}^{N-1}e^{ik\cdot r_j}q_j|j\rangle\right)\left|\frac{kM}{2\pi}\right\rangle|0\rangle \xrightarrow{\mathcal{F}_j}$$

$$\frac{1}{\sqrt{N}M^{3/2}}\sum_{k=0}^{K}\left(\sum_{t=0}^{N-1}\sum_{j=0}^{N-1}e^{ik\cdot r_j}e^{2\pi itj/N}q_j|t\rangle\right)\left|\frac{kM}{2\pi}\right\rangle|0\rangle = |\psi_F\rangle.$$

The transformations by the operations $\mathcal{F}_r$ and $\mathcal{F}_j$ can be implemented by the application of a combination of single-qubit gate operations and two-qubit gate operations by the system controller 104.

The computational complexity of the QFT scales as $\mathcal{O}(\Gamma \log \Gamma)$. Thus, the complexity of producing the Fourier transformed superposition state $|\psi_F\rangle$ from the initial superposition state $|\psi_S\rangle\mathcal{O}$ scales as $\mathcal{O}(\Gamma^2 + \Gamma \log \Gamma) = \mathcal{O}(\Gamma^2)$.

In block 816, by the system controller 104, amplitude of the final superposition state $|\psi_F\rangle A_F(k)$ (also referred to as "Fourier amplitude") is amplified and estimated. The amplitude of the final superposition state $|\psi_F\rangle$ is measured in the state $$|0\rangle \left| \frac{kM}{2\pi} \right\rangle |0\rangle$$

as $$A_F(k) = \langle 0| \left( \frac{kM}{2\pi} \middle| \langle 0\| \psi_F \rangle \right) = \frac{1}{NM^{3/2}} \left( \sum_{j=0}^{N-1} q_j e^{ik \cdot r_j} \right) = \frac{1}{NM^{3/2}} \hat{\rho}^q(k),$$

which is proportional to the electric form factor $\hat{\rho}^q(k)$ for k included in the long-range inter-particle interaction energies $U^{long}$.

The estimation of Fourier amplitudes can be performed by a known protocol for amplitude amplification and estimation. This protocol uses an iterative procedure to amplify the amplitude of a target state and can be implemented by use of a combination of single-qubit gate operations and two-qubit gate operations. To estimate the Fourier amplitudes $A_F(k)$ up to an error $\epsilon'$, steps similar to those described in blocks 810-814 are repeated $\mathcal{O}(1/\epsilon')$ times with additional $\mathcal{O}(\log(1/\epsilon'))$ qubits. Thus, the overall complexity of estimating the Fourier amplitude $A_F(k)$ scales as $\mathcal{O}(\Gamma^2/\epsilon')$.

In block 818, the estimated Fourier amplitudes $A_F(k)$ is returned to the classical computer 102. By the classical computer 102, modulus square of estimated Fourier amplitudes $A_F(k)$, $|A_F(k)|^2$, is computed and converted to be recorded for the purpose of computing of the long-range inter-particle interaction energies $U^{long}$. The process returns block 806 to select another reciprocal vector k if the modulus square of estimated Fourier amplitudes $A_F(k)$, $|A_F(k)|^2$ for sufficiently many reciprocal vectors k have not been computed.

In block 820, by the classical computer 102, a sum of the inter-particle interaction energies $U^{coul} = U^{short} + U^{long} + U^{self}$ is computed. The short-range inter-particle interaction energies $U^{short}$ and the self-energies $U^{self}$ have been computed by the classical computer 102 in block 804. The long-range inter-particle interaction energies $U^{long}$ can be calculated by the classical computer 102 using the estimated Fourier amplitudes $A_F(k)$ as $$U^{long} = \frac{2\pi \sqrt{N} M^{3/2}}{L^3} \sum_{k=0}^{K} \frac{1}{k^2} \exp\left(-\frac{k^2}{4\alpha^2}\right) |A_F(k)|^2.$$

In block 822, the classical computer 102 will typically output the computed sum of the inter-particle interaction energies $U^{coul} = U^{short} + U^{long} + U^{self}$ to a user interface, such as graphics processing unit (GPU), of the classical computer 102 and/or save the $U^{coul} = U^{short} + U^{long} + U^{self}$ in the memory of the classical computer 102.

The maximal k to be considered, i.e., K, is typically chosen to ensure the simulation is accurate to within the desired upper-bound error $\delta$. Optimizing K with respect to a desired upper-bound error $\delta$ in the MD simulation, the number of operations scales as $\mathcal{O}(N^{3/2})$ in the classical Ewald summation. In the quantum-classical hybrid approach, when optimizing K with respect to a desired upper-bound error $\delta$, the number of operations scales as $\mathcal{O}(N^{25/17}(\log N)^2)$, with $\epsilon' = \mathcal{O}(\delta/(K^d N^{1/2}))$, where d is the dimension of the system (e.g., d=3 for a 3 dimensional (3D) system) and $\Gamma = \mathcal{O}(\log(NK/\epsilon))$.

The method of obtaining energies of a system having interacting particles by molecular dynamics (MD) simulations described herein provides a complexity improvement by use of a quantum processor in the calculation of Ewald summation method over the classical calculation method.

It should be noted that the particular example embodiments described above are just some possible examples of a hybrid quantum-classical computing system according to the present disclosure and do not limit the possible configurations, specifications, or the like of hybrid quantum-classical computing systems according to the present disclosure. For example, the method described herein may be applied to other simulation problems such as simulation of trapped ions in a quantum computer to help design a better quantum computer. Furthermore, a quantum processor within a hybrid quantum-classical computing system is not limited to a group of trapped ions described above. For example, a quantum processor may be a superconducting circuit that includes micrometer-sized loops of superconducting metal interrupted by a number of Josephson junctions, functioning as qubits (referred to as flux qubits). The junction parameters are engineered during fabrication so that a persistent current will flow continuously when an external magnetic flux is applied. As only an integer number of flux quanta are allowed to penetrate in each loop, clockwise or counter-clockwise persistent currents are developed in the loop to compensate (screen or enhance) a non-integer external magnetic flux applied to the loop. The two states corresponding to the clockwise and counter-clockwise persistent currents are the lowest energy states; differ only by the relative quantum phase. Higher energy states correspond to much larger persistent currents, thus are well separated energetically from the lowest two eigenstates. The two lowest eigenstates are used to represent qubit states $|0\rangle$ and $|1\rangle$. An individual qubit state of each qubit device may be manipulated by application of a series of microwave pulses, frequency and duration of which are appropriately adjusted.

While the foregoing is directed to specific embodiments, other and further embodiments may be devised without departing from the basic scope thereof, and the scope thereof is determined by the claims that follow.

The invention claimed is:

1. A method of performing computation using a hybrid quantum-classical computing system comprising a classical computer and a quantum processor, comprising:

computing, by use of the classical computer and the quantum processor comprising a first register of a plurality of qubits, a second register of a plurality of qubits, and a third register of a plurality of qubits, multiple energies of a group of interacting particles of a molecular dynamics system that each have a particle index based on an Ewald summation method, the multiple energies comprising short-range inter-particle interaction energies, self-energies, and long-range inter-particle interaction energies, the computing of the multiple energies including:
    computing long-range inter-particle interaction energies based on Fourier transformations to the quantum processor, the computing of the long-range inter-particle interaction energies including:
        applying a first operation to the first register encoding the particle indices to transform the quantum processor from an initial state to an initial superposition state of the particle indices;
        applying a second operation to the second register encoding positions of the interacting particles, and a third operation to the third register encoding charges of the interacting particles to transform the quantum processor from the initial superposition state of the particle indices to an intermediate superposition state;
        applying a combination of single-qubit operations to the third register to transform the quantum processor from the intermediate superposition state to a phased intermediate superposition state, wherein the charges of the interacting particles are encoded in phases of the phased intermediate superposition state and the third register; and
        applying an inverse operation of the third operation to the third register to transform the quantum processor from the phased intermediate superposition state to a charge-position encoded state; and
    outputting, by use of the classical computer, the computed sum of the short-range inter-particle interaction energies, the self-energies of the system, and the long-range inter-particle interaction energies as a total inter-particle interaction energies of the molecular dynamics system.

2. The method according to claim 1, wherein:
the computing of the multiple energies further includes computing the short-range inter-particle interaction energies and the self-energies,
the computing of the long-range inter-particle interaction energies further includes:
    transforming the quantum processor from the charge-position encoded state to a Fourier transformed superposition state; and
    measuring an estimated amplitude of the Fourier transformed superposition state on the quantum processor,
the computing of the multiple energies further includes:
    computing long-range inter-particle interaction energies based on the measured estimated amplitude of the Fourier transformed superposition state; and
    computing, by use of the classical computer, a sum of the short-range inter-particle interaction energies, the self-energies of the system, and the long-range inter-particle interaction energies.

3. The method according to claim 2, wherein
the quantum processor comprises a group of trapped ions, each of which has two frequency-separated states defining a qubit, and
computing of the long-range inter-particle interaction energies further includes preparing the quantum processor in the initial state by setting, by a system controller, each trapped ion in the quantum processor in a superposition of the two frequency-separated states.

4. The method according to claim 1, wherein transforming the quantum processor from the initial state to the charge-position encoded state comprises applying, by use of a system controller, a combination of gate operations to the quantum processor.

5. The method according to claim 4, wherein the combination of gate operations comprises single-qubit gate operations and two-qubit gate operations.

6. The method according to claim 2, wherein transforming the quantum processor from the charge-position encoded state to the Fourier transformed superposition state comprises applying, by use of a system controller, a combination of single-qubit operations and two-qubit operations to the quantum processor.

7. A hybrid quantum-classical computing system, comprising:
    a quantum processor comprising a first register of a plurality of a plurality of qubits, a second register of a plurality of qubits, and a third register of a plurality of qubits, each qubit defined by two hyperfine states of a trapped ion;
    one or more lasers configured to emit a laser beam, which is provided to trapped ions in the quantum processor;
    a classical computer configured to:
        compute multiple energies of a group of interacting particles of a molecular dynamics system that each have a particle index based on an Ewald summation method, the multiple energies comprising short-range inter-particle interaction energies, self-energies, and long-range inter-particle interaction energies, the computing of the multiple energies including:
    computing long-range inter-particle interaction energies based on Fourier transformations to the quantum processor, the computing of the long-range inter-particle interaction energies including:
        applying a first operation to the first register encoding the particle indices to transform the quantum processor from an initial state to an initial superposition state of the particle indices;
        applying a second operation to the second register encoding positions of the interacting particles, and a third operation to the third register encoding charges of the interacting particles to transform the quantum processor from the initial superposition state of the particle indices to an intermediate superposition state;
        applying a combination of single-qubit operations to the third register to transform the quantum processor from the intermediate superposition state to a phased intermediate superposition state, wherein the charges of the interacting particles are encoded in phases of the phased intermediate superposition state and the third register; and
        applying an inverse operation of the third operation to the third register to transform the quantum processor from the phased intermediate superposition state to a charge-position encoded state; and
    output the computed sum of the short-range inter-particle interaction energies, the self-energies of the system, and the long-range inter-particle interaction energies as a total inter-particle interaction energies of the molecular dynamics system; and
a system controller configured to control the emission of the laser beam from the one or more lasers.

8. The hybrid quantum-classical computing system according to claim 7, wherein
the computing of the multiple energies further includes:
computing the short-range inter-particle interaction energies and the self-energies,
the system controller is further configured to:
transform the quantum processor from the charge-position encoded state to a Fourier transformed superposition state; and
measure an estimated amplitude of the Fourier transformed superposition state on the quantum processor, and
the computing of the multiple energies further includes:
computing long-range inter-particle interaction energies based on the measured estimated amplitude of the Fourier transformed superposition state; and
computing a sum of the short-range inter-particle interaction energies, the self-energies of the group of the interacting particles, and the long-range inter-particle interaction energies.

9. The hybrid quantum-classical computing system according to claim 8, wherein
the quantum processor is set in the initial state by setting each trapped ion in the quantum processor in a lower state of the two hyperfine states using optical pumping, and
the system controller is further configured to prepare the quantum processor in the initial state by setting each trapped ion in the quantum processor in a superposition of the two hyperfine states.

10. The hybrid quantum-classical computing system according to claim 7, wherein the system controller transforms the quantum processor from the initial state to the charge-position encoded state by applying a combination of gate operations to the quantum processor.

11. The hybrid quantum-classical computing system according to claim 10, wherein the combination of gate operations comprises single-qubit gate operations and two-qubit gate operations.

12. The hybrid quantum-classical computing system according to claim 8, wherein the system controller transforms the quantum processor from the charge-position encoded state to the Fourier transformed superposition state by applying a combination of single-qubit operations and two-qubit operations to the quantum processor.

13. A hybrid quantum-classical computing system comprising:
a classical computer;
a quantum processor comprising a first register of a plurality of qubits, a second register of a plurality of qubits, and a third register of a plurality of qubits; and
non-volatile memory having a number of instructions stored therein which, when executed by one or more processors, causes the hybrid quantum-classical computing system to perform operations comprising:
computing, by use of the classical computer and the quantum processor, multiple energies of a group of interacting particles of a molecular dynamics system that each have a particle index based on an Ewald summation method, the multiple energies comprising short-range inter-particle interaction energies, self-energies, and long-range inter-particle interaction energies, the computing of the multiple energies including:
computing long-range inter-particle interaction energies based on Fourier transformations to the quantum processor, the computing of the long-range inter-particle interaction energies including:
applying a first operation to the first register encoding the particle indices to transform the quantum processor from an initial state to an initial superposition state of the particle indices;
applying a second operation to the second register encoding positions of the interacting particles, and a third operation to the third register encoding charges of the interacting particles to transform the quantum processor from the initial superposition state of the particle indices to an intermediate superposition state;
applying a combination of single-qubit operations to the third register to transform the quantum processor from the intermediate superposition state to a phased intermediate superposition state, wherein the charges of the interacting particles are encoded in phases of the phased intermediate superposition state and the third register; and
applying an inverse operation of the third operation to the third register to transform the quantum processor from the phased intermediate superposition state to a charge-position encoded state; and
outputting, by use of the classical computer, the computed sum of the short-range inter-particle interaction energies, the self-energies of the system, and the long-range inter-particle interaction energies as a total inter-particle interaction energies of the molecular dynamics system.

14. The hybrid quantum-classical computing system according to claim 13, wherein
the computing of the multiple energies further includes computing the short-range inter-particle interaction energies and the self-energies, the long-range inter-particle interaction energies further includes:
transforming the quantum processor from the charge-position encoded state to a Fourier transformed superposition state; and
measuring an estimated amplitude of the Fourier transformed superposition state on the quantum processor, and
the computing of the multiple energies further includes:
computing, by use of the classical computer, long-range inter-particle interaction energies based on the measured estimated amplitude of the Fourier transformed superposition state; and
computing, by use of the classical computer, a sum of the short-range inter-particle interaction energies, the self-energies of the group of the interacting particles, and the long-range inter-particle interaction energies.

15. The hybrid quantum-classical computing system according to claim 14, wherein
the quantum processor comprises a group of trapped ions, each of which has two frequency-separated states defining a qubit, and
the long-range inter-particle interaction energies further includes preparing the quantum processor in the initial state by setting, by a system controller, each trapped ion in the quantum processor in a superposition of the two frequency-separated states.

16. The hybrid quantum-classical computing system according to claim 13, wherein transforming the quantum processor from the initial state to the charge-position encoded state comprises applying, by a system controller, a combination of gate operations to the quantum processor.

17. The hybrid quantum-classical computing system according to claim 14, wherein transforming the quantum processor from the charge-position encoded state to the Fourier transformed superposition state comprises applying, by a system controller, a combination of single-qubit operations and two-qubit operations to the quantum processor.

\* \* \* \* \*